(12) United States Patent
Todd

(10) Patent No.: US 6,733,830 B2
(45) Date of Patent: May 11, 2004

(54) PROCESSES FOR DEPOSITING LOW DIELECTRIC CONSTANT MATERIALS

(75) Inventor: Michael A. Todd, Phoenix, AZ (US)

(73) Assignee: ASM Japan K.K. (JP)

( * ) Notice: Subject to any disclaimer, the term of this patent is extended or adjusted under 35 U.S.C. 154(b) by 542 days.

(21) Appl. No.: 09/779,397

(22) Filed: Feb. 7, 2001

(65) Prior Publication Data

US 2001/0055672 A1 Dec. 27, 2001

Related U.S. Application Data

(60) Provisional application No. 60/192,115, filed on Mar. 24, 2000, provisional application No. 60/180,863, filed on Feb. 8, 2000, provisional application No. 60/180,865, filed on Feb. 8, 2000, provisional application No. 60/180,883, filed on Feb. 8, 2000, provisional application No. 60/180,884, filed on Feb. 8, 2000, provisional application No. 60/180,885, filed on Feb. 8, 2000, and provisional application No. 60/180,946, filed on Feb. 8, 2000.

(51) Int. Cl.$^7$ .............................................. C23C 16/24
(52) U.S. Cl. ........................... 427/255.28; 427/255.29; 427/255.395
(58) Field of Search ....................... 427/255.28, 255.29, 427/255.395

(56) References Cited

U.S. PATENT DOCUMENTS

| | | | |
|---|---|---|---|
| 4,781,942 A | | 11/1988 | Leyden et al. |
| 4,863,755 A | | 9/1989 | Hess et al. |
| 4,894,352 A | | 1/1990 | Lane et al. |
| 4,992,306 A | | 2/1991 | Hochberg et al. |
| 5,011,706 A | | 4/1991 | Tarhay et al. |
| 5,028,566 A | | 7/1991 | Lagendijk |
| 5,231,058 A | | 7/1993 | Maeda et al. |
| 5,240,813 A | | 8/1993 | Watanabe et al. |
| 5,314,724 A | | 5/1994 | Tsukune et al. |
| 5,324,539 A | | 6/1994 | Maeda et al. |
| 5,380,555 A | | 1/1995 | Mine et al. |
| 5,433,786 A | | 7/1995 | Hu et al. |
| 5,494,712 A | | 2/1996 | Hu et al. |
| 5,554,570 A | | 9/1996 | Maeda et al. |
| 5,563,105 A | | 10/1996 | Dobuzinsky et al. |
| 5,703,404 A | | 12/1997 | Matsuura |
| 5,840,821 A | | 11/1998 | Nakano et al. |
| 5,876,798 A | | 3/1999 | Vassiliev |
| 5,989,998 A | | 11/1999 | Sugahara et al. |
| 5,998,522 A | | 12/1999 | Nakano et al. |
| 6,004,730 A | * | 12/1999 | Mikoshiba et al. ......... 430/325 |
| 6,045,877 A | | 4/2000 | Gleason et al. |
| 6,051,321 A | | 4/2000 | Lee et al. |
| 6,051,508 A | | 4/2000 | Takase et al. |
| 6,054,379 A | | 4/2000 | Yau et al. |
| 6,068,884 A | | 5/2000 | Rose et al. |
| 6,245,690 B1 | * | 6/2001 | Yau et al. .................... 438/780 |
| 6,258,407 B1 | * | 7/2001 | Lee et al. .............. 427/255.28 |
| 6,303,047 B1 | * | 10/2001 | Aronowitz et al. ............. 252/1 |
| 6,340,628 B1 | * | 1/2002 | Van Cleemput et al. .... 438/586 |
| 6,458,718 B1 | * | 10/2002 | Todd .......................... 438/778 |

FOREIGN PATENT DOCUMENTS

| | | |
|---|---|---|
| EP | 0 706 216 A2 | 4/1998 |
| WO | WO 97/41592 | 11/1997 |
| WO | WO 99/21706 | 5/1999 |
| WO | WO 99/41423 | 8/1999 |
| WO | WO 99/60621 | 11/1999 |

OTHER PUBLICATIONS

Varma, Ravi, "Organosilyation: Synthesis and Characterization of Silymethyl Methyl Ether," Inorg. Nucl. Chem. Letters, vol. 6, pp. 9–14, 1970.

Bayer et al., *Overall kinetics of SiOx remote–PECVD using different organosilicon monomers*, Surface and Coatings Technology, 116–119 (1999) 874–878.

Berjoan et al., *XPS and XPS valence band characterizations of amorphous or polymeric silicon based thin films prepared by PACVD from organosilicon monomers*, J. Phys. IV France 9 (1999) pp. 1059–1068.

Constant et al., *Some Properties of amorphous SiXc1–x (H) alloys prepared by CVD from various organosilicon compounds*, Solid State Chemistry, 1982, pp. 267–270.

Deville et al., *An AES study of the Influence of carbon on the chemical structure of some oxide films deposited by PECVD of organosilicon precursors*, Applied Surface Science 137 (1999) 136–141.

Fonseca et al., *Plasma Polymerization of TetrameThyisilane*, Am. Chemical Society, 1993, 5, 1676–1682.

Inoue et al., *Mass spectroscopy in plasma–enhanced chemical vapor deposition of silicon–oxide films using tetramethoxyisilane*, Thin Solid Films 316 (1998) 79–84.

Inoue et al., *Spectroscopic studies on preparation of silicon oxide films by PECVD using organosilicon compounds*, Plasma Sources Sci. Technol, 5 (1995) 339–343.

Loboda, M.J., *New solutions for intermeial dielectrics using trimelhylsilane–based PECVD processes*, Microelectronic Enginering 50 (20000) 15–23.

Nguyen et al., *Plasma organosilicon polymers*, J. Electrochem. Soc., Aug. 1985, pp. 1925–1932.

Shirafuji et al., *PE–CVD of Fluorocarbon/SiO composite thin films using C4F8 and HMDSO1*, Plasmas and Polymers, Vo. 4, No. 1, 1999, pp. 57–75.

(List continued on next page.)

*Primary Examiner*—Bret Chen
(74) *Attorney, Agent, or Firm*—Knobbe Martens Olson & Bear LLP

(57) ABSTRACT

Chemical vapor deposition processes result in films having low dielectric constants when suitable chemical precursors are utilized. Preferred chemical precursors include siloxanes, (fluoroalkyl)fluorosiloxanes, (fluoroalkyl)silanes, (alkyl)fluorosilanes, (fluoroalkyl)fluorosilanes, alkylsiloxysilanes, alkoxysilanes, alkylalkoxysilanes, silylmethanes, alkoxysilylmethanes, alkylalkoxysilylmethanes, alkoxymethanes, alkylalkoxymethanes, and mixtures thereof. The precursors are particularly suited to thermal CVD for producing low dielectric constant films at relatively low temperatures, particularly without the use of additional oxidizing agents. Such films are useful in the microelectronics industry.

45 Claims, 4 Drawing Sheets

OTHER PUBLICATIONS

Shirafuji et al., *PE–CVD of fluorocarbon/silicon oxide composite thin films from TFE and HMDSO*, Mat. Res. Soc. Symp. Proc. vol. 544, pp. 173–178 1999.

Shirafuji et al., *Plasma copolymerization of tetrafluoroethylene/hexamethyldisiloxane and In Situ Fourier Transform infrared spectroscopy of its gas phase*, Jpn. J. Appl. Phys. vol. 38 (1999) pp. 4520–4526.

Sugahara et al., *Low Dielectric constant carbon containing SiO2 films deposited by PECVD technique using a novel CVD precursor*, DUMIC Conference, Feb. 10–11, 1997, pp. 19–25.

Thomas et al. *Plasma etching and surface analysis of a SiC:H films deposited by low temperature plasma enhanced chemical vapor deposition*, Mat. Res. Soc. Symp. Proc. Vo. 334, 1994, pp. 445–450.

Indrajit Banerjee, et al., "Characterization of Chemical Vapor Deposited Amorphous Fluorocarbons for Low Dielectric Constant Interlayer Dielectrics." J. Electrochem. Soc., vol. 146(6), p. 2219 (1999).

Sang–Soo Han, et al., "Deposition of Fluorinated Amorphous Carbon Thin Films as a Low–Dielectric Constant Material." J. Electrochem. Soc., vol. 146(9), p. 3383 (1999).

H. Beckers, et al., "Synthesis and Properties of (Triflouromethyl) trichlorosilane, a Versatile Precursor for CF3SI Compounds," J. Organometal. Chem., vol. 316, pp. 41–50, (1986).

C.A. Costello and J.J. McCarthy, "Introduction of Organic Functional Groups onto the Surface of Poly(tetrafluoreothylene)," Proceedings of the ACS Division of Polymeric Materials Science and Engineering, vol. 55 p. 893 (1986).

K.G. Sharp and T.D. Coyle, "Synthesis and Some Properties of Trifluoro(trifluoromethyl) silane," J. Fluorine Chem., vol. Q. pp. 249–251 (1971/72).

Limb, Scott J., et al., "Growth of fluorcarbon polymer thin films with high CF2 fractions and low dangling bond concentrations by thermal chemical vapor deposition," App. Phys. Lett., vol. 68(20), p. 2810 (1996).

Washbume, Stephen S., et al. "Chloraminosilanes: I: The Preparation of Chloro(Dimethylamino) Hydrogen Silanes," Inorg. Nucl. Chem. Letters vol. 5, pp. 17–19, Pergaomon Press, 1969.

Savage, Charles R., et al., "Spectroscopic Characterization of Films Obtained in Pulsed Radio–Frequency Plasma Discharges of Fluorocarbon Monomers," Structure–Property Relations In Polymers, pp. 745–768, American Chemical Society, (1993).

Sharp, K.G., et al., "Perflouro(alkylsilanes). II: Trifluoro(t-rifluoromethyl) silane and Trifluoro)pentafluoroethyl) silane," Inorg. Chem., vol. 11, No. 6, pp. 1259–1264, 1972.

Patent Abstracts of Japan vol. 1998, No. 03, Feb. 27, 1998 & JP 09 293716 A (Kawasaki Steel Corp), Nov. 11, 1997.

Patent Abstracts of Japan vol. 1999, No. 12, Oct. 29, 1999 & JP 11 176829 A (Innotech Corp), Jul. 2, 1999 *abstract*.

Chandrasekhar et al., "New Silicon–Carbon Materials Incorporating $Si_4C$ Building Blocks" Mat. Res. Soc. Symp. Proc. vol. 441, Materials Research Society (1997).

* cited by examiner

PROCESSES FOR DEPOSITING LOW DIELECTRIC CONSTANT MATERIALS

RELATED APPLICATION INFORMATION

This application claims priority under 35 U.S.C. §119(e) to the following U.S. provisional applications: Serial No. 60/180,863, filed Feb. 8, 2000; Serial No. 60/180,865, filed Feb. 8, 2000; Serial No. 60/180,883, filed Feb. 8, 2000; Serial No. 60/180,884, filed Feb. 8, 2000; Serial No. 60/180,885, filed Feb. 8, 2000; Serial No. 60/180,946, filed Feb. 8, 2000; and Serial No. 60/192,115, filed Mar. 24, 2000; each of which is hereby incorporated by reference in its entirety.

BACKGROUND OF THE INVENTION

1. Field of the Invention

This invention relates generally to low dielectric constant ("low-k") materials, and more particularly to chemical vapor deposition (CVD) processes for making low-k materials, and the use of low-k materials as dielectric layers in microelectronic devices.

2. Description of the Related Art

As the dimensions of microelectronic devices become smaller, the importance of the physical properties of the materials used in their manufacture becomes more important. This is particularly true of the dielectric materials that are used to insulate metal lines and vias from one another because of the contributions to parasitic capacitance that these materials make. Silicon dioxide has been employed within the industry as a dielectric material for the manufacture of devices for nearly three decades, but may become less suitable in the future because of its relatively high dielectric constant (k~4.1). Thus, there is a need in the art of microelectronic device manufacturing for a process to deposit low-k films.

Fluorinated silicon glass (FSG) has been identified as a possible replacement for silicon dioxide, see e.g., U.S. Pat. Nos. 5,563,105; 5,703,404; and 5,876,798. FSG films are known to have a dielectric constant in the range 3.3 to 3.6, depending on the fluorine concentration.

Carbon is also known to reduce the dielectric constant of oxide materials. Generally speaking, organic precursors are employed in plasma deposition or spin-on deposition processes. The preparation of low-k films by plasma-enhanced chemical vapor deposition (PECVD) has been disclosed, for example in G. Sugahara et al., "Low Dielectric Constant Carbon Containing $SiO_2$ Films Deposited By PECVD Technique Using a Novel CVD Precursor," Feb. 10–11, 1997, DUMIC Conference, 97ISMIC-222D; T. Shirafuji et al., "Plasma Copolymerization of Tetrafluoroethylene/Hexamethyldisiloxane and In Situ Fourier Transform Infrared Spectroscopy of Its Gas Phase," Jpn. J. Appl. Phys., 38, 4520–26 (1999); M. Loboda, "New solutions for intermetal dielectrics using trimethylsilane-based PECVD processes," Microelectronic Engineering, 50, 15–23 (2000); T. Shirafuji et al., "PE-CVD of Fluorocarbon/SIO Composite Thin Films Using C4H8 and HMDSO," Plasmas and Polymers, 4(1) 57–75 (1999); T. Shirafuji et al., "PE-CVD of Fluorocarbon/Silicon Oxide Composite Thin Films from TFE and HMDSO," Mat. Res. Soc. Symp. Proc., 544, 173–178 (1999). Other references in this regard include Indrajit Banerjee, et. al., "Characterization of Chemical Vapor Deposited Amorphous Fluorocarbons for Low Dielectric Constant Interlayer Dielectrics." J. Electrochem. Soc., Vol. 146(6), p. 2219, 1999; C. B. Labelle, et. al., DUMIC, pg. 1998, 1997; Sang-Soo Han, et. al., "Deposition of Fluorinated Amorphous Carbon Thin Films as a Low-Dielectric Constant Material." J. Electrochem. Soc., Vol. 146(9), p. 3383, 1999; U.S. Pat. Nos. 6,068,884; 6,051,321; 5,989,998; and 5,900,290. All patents and literature references mentioned herein are incorporated by reference in their entireties.

Spin-on processes are also known for making low-k films. These processes generally involve dissolving or dispersing a low-k polymer in a solvent to form a liquid coating mixture, depositing the coating mixture onto a substrate, spinning the substrate to create a uniform coating, then drying the coating to remove the solvent. Another known method for reducing the dielectric constant of a film is to introduce porosity into the film.

There remains a need for low-k films having better properties more suitable for use in microelectronics manufacturing, and for processes for producing such films that can be readily integrated into fabrication process flows.

SUMMARY OF THE INVENTION

Available processes for the deposition of low-k films may be suitable in some semiconductor manufacturing processes, but there is a need in the art for CVD processes that do not require the use of a plasma. Thus far, that need has not been fulfilled by thermal CVD processes because films deposited using conventional chemical precursors do not have the desired low dielectric constant, or because thermal CVD of those precursors must be conducted at a temperature that is too high for the stage of the integrated circuit production. Accordingly, there is a need in the art for chemical precursors that can be used to produce low-k films by thermal CVD. Preferably, these chemicals precursors would be highly versatile, forming low-k films under a variety of CVD conditions, thus providing the manufacturer with a range of processing options for a given application.

The inventor has discovered a number of chemical precursors that are useful in CVD processes for the deposition of low-k films.

In one embodiment, a thermal chemical vapor deposition process for depositing a Si-containing material on a surface is provided. In this preferred process, a substrate is contained in a chemical vapor deposition chamber and a gas containing a chemical precursor is introduced to the chamber. The chemical precursor is preferably a compound containing at least one silicon atom and at least one carbon atom, or a compound containing at least one carbon atom and at least one oxygen atom. The chemical precursor is more preferably a siloxane, a (fluoroalkyl)fluorosiloxane, a (fluoroalkyl)silane, an (alkyl)fluorosilane, a (fluoroalkyl)fluorosilane, an alkylsiloxysilane, an alkoxysilane, an alkylalkoxysilane, a silylmethane, an alkoxysilylmethane, an alkylalkoxysilylmethane, an alkoxymethane, an alkylalkoxymethane, or a mixture of two or more of these chemical precursors with one another. The Si-containing film is preferably deposited onto the substrate by thermal CVD at a temperature of about 300° C. or higher, and preferably has a dielectric constant of about 3.5 or lower, as deposited. These Si-containing films are useful in the manufacture of integrated circuits, e.g., as interlevel dielectrics.

In another preferred embodiment, a CVD process is provided for depositing a low-k Si-containing material on a surface. In a preferred CVD process, a substrate is contained in a chemical vapor deposition chamber and a gas containing a chemical precursor is introduced to the chamber. The chemical precursor is preferably a silylmethane, an alkoxysilylmethane, an alkylalkoxysilylmethane, an alkoxymethane, an alkylalkoxymethane, or a mixture of two or more these chemical precursors with one another. The Si-containing film is preferably deposited onto the substrate by thermal CVD, and the film preferably has a dielectric constant of about 3.5 or lower, as deposited. These processes are useful for making Si-containing films with utility in the manufacture of integrated circuits, e.g., as interlevel dielectrics.

In another preferred embodiment, novel alkoxysilylmethanes and alkylalkoxysilylmethanes are provided, useful as chemical precursors for low-k films, as well as processes for making them.

Multi-layered low-k films and processes for making them are also disclosed herein.

In a preferred embodiment, a CVD process for depositing a Si-containing material on a surface is provided. In a preferred CVD process, a substrate is contained in a chemical vapor deposition chamber and a first gas containing a first chemical precursor is introduced to the chamber. A first Si-containing film is deposited onto the substrate. This first Si-containing film preferably has a dielectric constant of about 3.5 or lower, as deposited, and a thickness in the range of about 50 Å to about 5000 Å. A second gas containing a second chemical precursor, different from the first chemical precursor, is then introduced into the chamber, and a multi-layered film is created by depositing a second Si-containing film onto the first film. This second Si-containing film preferably has a dielectric constant of about 3.5 or lower, as deposited, and a thickness in the range of about 50 Å to about 5000 Å. The resulting multi-layered film preferably has a dielectric constant of about 3.5 or lower, as deposited. Preferably, the outer layers of the multi-layer film have good adhesion and the inner layer(s) have a low dielectric constant. Preferably, at least one layer of the multi-layered film is deposited by thermal CVD.

In another preferred embodiment, the process is continued by introducing a third gas, comprised of a third chemical precursor, to the chamber and depositing a third Si-containing film onto the second Si-containing film. Preferably, this third Si-containing film has a dielectric constant of about 3.5 or lower, as deposited, and a thickness in the range of about 50 Å to about 5000 Å.

In another embodiment, multi-layered films are provided, preferably made by the processes described above. A preferred multi-layered film contains at least a first layer and a second layer, wherein the first layer contains of an amount of silicon in the range of about 1% to about 60%, an amount of carbon in the range of about 10% to about 90%, an amount of oxygen in the range of 0% to about 35%, and an amount of fluorine in the range of 0% to about 67%, each by weight based on total weight; and the second layer contains an amount of silicon in the range of about 1% to about 50%, an amount of carbon in the range of about 10% to about 60%, an amount of oxygen in the range of 0% to about 30%, and an amount of fluorine in the range of 0% to about 67%, each by weight based on total weight. These multi-layered films are useful in the manufacture of integrated circuits, e.g., as interlevel dielectrics.

These and other embodiments are described in greater detail below.

DETAILED DESCRIPTION OF THE PREFERRED EMBODIMENTS

Figure 1:
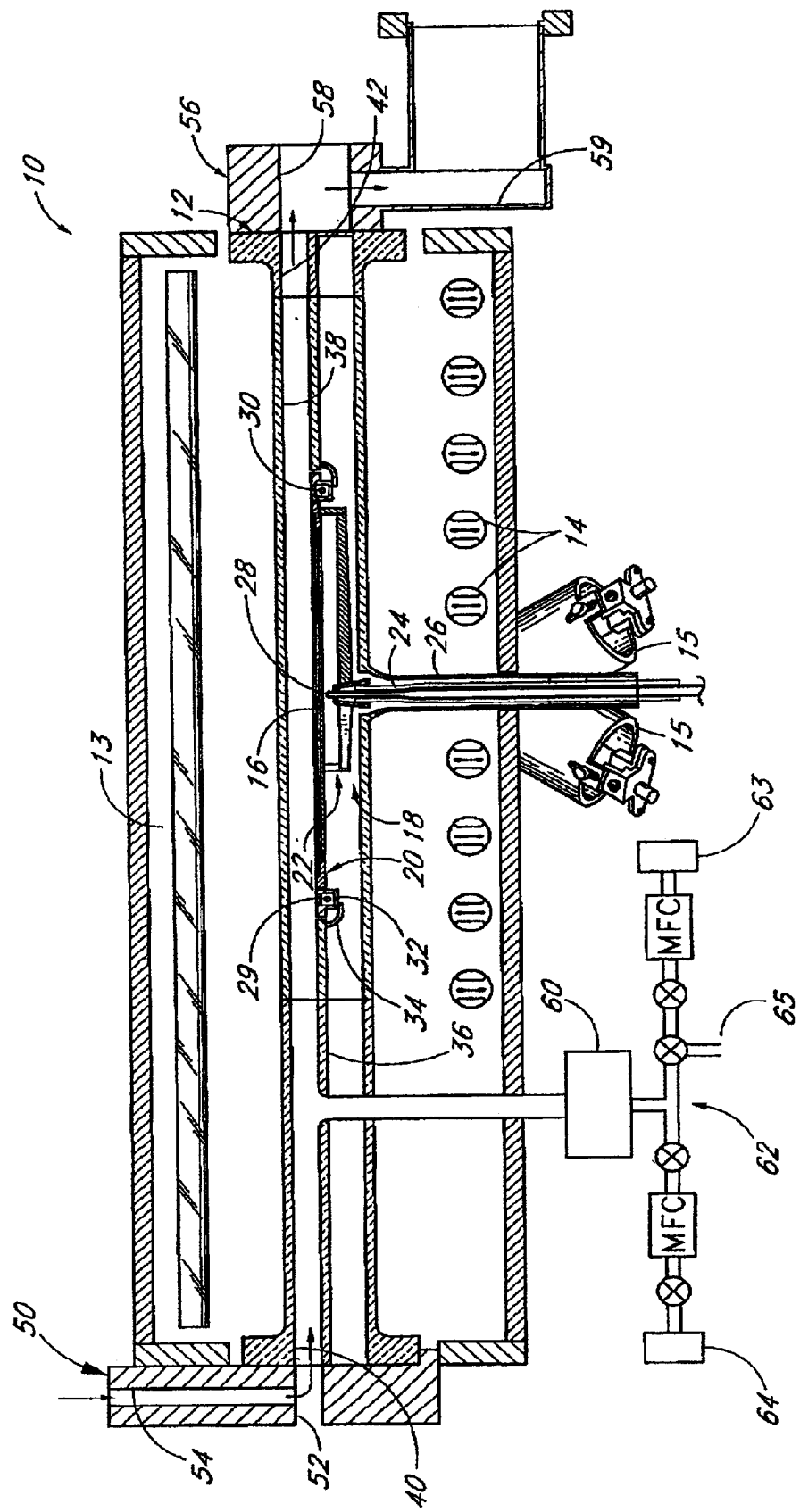
FIG. 1 is a schematic illustrating a chemical vapor deposition system for use with the preferred embodiments.

The chemical vapor deposition (CVD) processes of the preferred embodiments can be conducted using any suitable CVD system. A schematic diagram (not to scale) of a preferred thermal CVD system 10 is shown in FIG. 1. While originally designed to optimize epitaxial deposition of silicon on a single substrate at a time, the superior processing control has been found to have utility in a number of different materials. The basic configuration of the device 10 is available commercially under the trade name Epsilon® from ASM America, Inc. of Phoenix, Ariz.

The system 10 includes a quartz reaction or production chamber 12. A plurality of radiant heat sources are supported outside the chamber to provide heat energy to the chamber 12 without appreciable absorption by the quartz chamber 12 walls. While the preferred embodiments are described in the context of a "cold wall" CVD reactor for processing semiconductor wafers, it will be understood that the processing methods described herein will have utility in conjunction with other heating/cooling systems, such as those employing inductive or resistive heating.

The illustrated radiant heat sources comprise an upper heating assembly of elongated tube-type radiant heating elements 13. The upper heating elements 13 are preferably disposed in spaced-apart parallel relationship and also substantially parallel with the reactant gas flow path through the underlying reaction chamber 12. A lower heating assembly comprises similar elongated tube-type radiant heating elements 14 below the reaction chamber 12, preferably oriented transverse to the upper heating elements 13. Desirably, a portion of the radiant heat is diffusely reflected into the chamber 12 by rough specular reflector plates above and below the upper and lower lamps 13, 14, respectively. Additionally, a plurality of spot lamps 15 supply concentrated heat to the underside of the wafer support structure (described below), to counteract a heat sink effect created by cold support structures extending through the bottom of the reaction chamber 12.

A substrate, preferably comprising a silicon wafer 16, is shown supported within the reaction chamber 12 upon a substrate or wafer support structure 18. Note that while the substrate of the illustrated embodiment is a single crystal silicon wafer, it will be understood that the term "substrate" broadly refers to any surface on which a layer is to be deposited, as discussed elsewhere herein.

The illustrated support structure 18 includes a wafer holder 20, upon which the wafer 16 rests, and a support spider 22. The spider 22 is mounted to a shaft 24, which extends downwardly through a tube 26 depending from the chamber 12 lower wall. Preferably, the tube 26 communicates with a source of purge gas which can flow during processing, inhibiting process gases from escaping to backside of the wafer 16.

A plurality of temperature sensors are positioned in proximity to the wafer 16. The temperature sensors may take any of a variety of forms, such as optical pyrometers or thermocouples. The number and positions of the temperature sensors are selected to promote temperature uniformity.

In system 10, the temperature sensors comprise thermocouples, including a first or central thermocouple 28, suspended below the wafer holder 20 in any suitable fashion. The illustrated central thermocouple 28 passes through upon the spider 22 in proximity to the wafer holder 22. The system 10 further includes a plurality of secondary or peripheral thermocouples, also in proximity to the wafer 16, including a leading edge or front thermocouple 30, a trailing edge or rear thermocouple 31, and a side thermocouple 31 (not shown). Each of the peripheral thermocouples are housed within a slip ring 32 which surrounds the wafer holder 20 and wafer 16. Each of the central and peripheral thermocouples are connected to a temperature controller (not shown), which sets the power of the various heating elements 14 in response to the readings of the thermocouples.

In addition to housing the peripheral thermocouples, the slip ring 32 absorbs and emits radiant heat during high temperature processing, such that it compensates for a tendency toward greater heat loss or absorption at wafer edges, a phenomenon which is known to occur due to a greater ratio of surface area to volume in regions near such edges. By minimizing edge losses and the attending radial temperature non-uniformities across the wafer 16, the slip ring 32 can reduce the risk of crystallographic slip. The slip ring 32 can be suspended by any suitable means. For example, the illustrated slip ring 32 rests upon elbows 34 which depend from a front chamber divider 36 and a rear chamber divider 38. The dividers 36, 38 desirably are formed of quartz.

The illustrated reaction chamber 12 includes an inlet port 40 for the introduction of chemical precursor-containing gases and carrier gases, and the wafer 16 can also be received therethrough. An outlet port 42 is on the opposite side of the chamber 12, with the wafer support structure 18 positioned between the inlet 40 and outlet 42.

An inlet component 50 is fitted to the reaction chamber, adapted to surround the inlet port 40, and includes a horizontally elongated slot 52 through which the wafer 16 can be inserted. A generally vertical inlet 54 receives chemical precursor-containing gases from remote sources, as will be described more fully with respect to FIG. 2, and communicates such gases with the slot 52 and the inlet port 40. The inlet 54 can include gas injectors as described in U.S. Pat. No. 5,221,556, issued Hawkins et al., or as described with respect to FIGS. 21–26 in U.S. patent application Ser. No. 08/637,616, filed Apr. 25, 1996, the disclosures of which are hereby incorporated by reference. Such injectors are designed to maximize uniformity of gas flow for the single-wafer reactor.

An outlet component 56 similarly mounts to the process chamber 12 such that an exhaust opening 58 aligns with the outlet port 42 and leads to exhaust conduits 60. The conduits 60, in turn, communicate with suitable vacuum means (not shown) for drawing gases through the chamber 12.

Wafers are preferably passed from a handling chamber (not shown), which is isolated from the surrounding environment, through the slot 52 by a pick-up device. While a fork or paddle can serve as the handling device, the preferred pick-up device comprises a wand which shoots high velocity streams of gas at angles, as described in U.S. Pat. No. 4,846,102, the disclosure of which is hereby incorporated by reference. When brought close to the top of a wafer surface, the gas streams create a low pressure zone above the wafer, causing the wafer to lift. The handling chamber and the processing chamber 12 are preferably separated by a gate valve (not shown) of the type disclosed in U.S. Pat. No. 4,828,224, the disclosure of which is hereby incorporated by reference.

Figure 2:
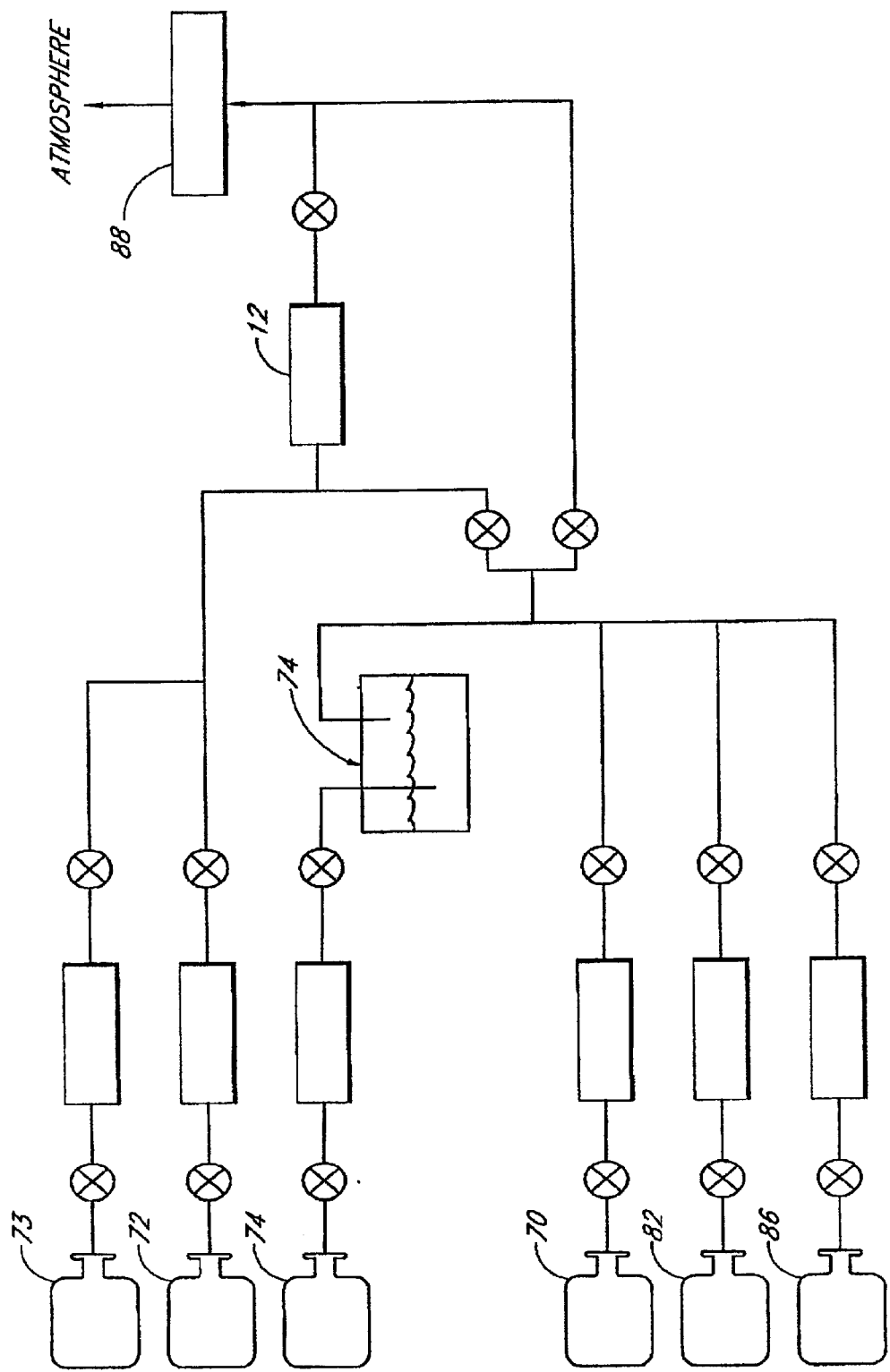
FIG. 2 is a gas line schematic illustrating the introduction of gases to the reactor in FIG. 1.

FIG. 2 shows a gas line schematic, in accordance with the preferred embodiment. The reaction chamber 12 is provided with a source 72 of a first carrier gas and a source 73 of a second carrier gas. Use of a second carrier gas is optional. Reaction chamber 12 is also provided with chemical precursors from sources 70, 71, 82 and 86. Each of the gas sources may be connected to the inlet 54 (FIG. 1) via gas lines with attendant safety and control valves, as well as mass flow controllers ("MFCs") which are coordinated at a gas panel. In the illustrated embodiment, source 71 is a bubbler which contains a chemical precursor through which a carrier gas supplied from source 74 is bubbled. The use of a bubbler is preferred when the source is a liquid. Gases are communicated to the inlet 54 (FIG. 1) in accordance with directions programmed into a central controller and distributed into the process chamber 12 through injectors. After passing through the process chamber, any unreacted chemical precursors or reaction by-products are exhausted through a pump 88. Preferably, the exhaust system also includes a scrubber (not shown) to condense environmentally dangerous fumes before exhausting to the atmosphere.

Figure 3:
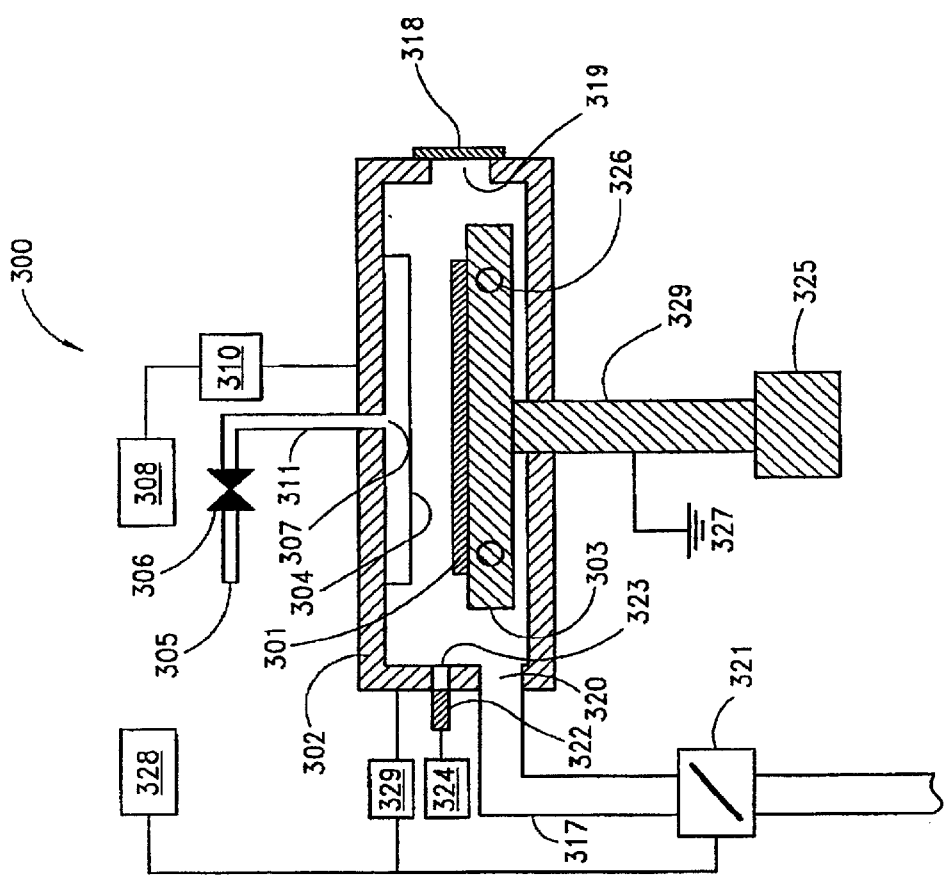
FIG. 3 is a schematic illustrating another chemical vapor deposition system.

PECVD can also be used to deposit the chemical precursors described herein. An exemplary PECVD reactor is and Eagle™ reactor, available commercially from ASM Japan K. K., Tokyo, Japan. The Eagle™ reactor is optimized for PECVD, but can also be used to deposit films by thermal CVD in accordance with the preferred embodiments. FIG. 3 is a schematic cross section of an exemplary plasma CVD device according to this embodiment. A plasma CVD device 300, which is used to form a thin film on a semiconductor wafer 301 or other substrate, comprises a reaction chamber 302, a support 303 provided within the reaction chamber to support the semiconductor wafer 301, a showerhead 304 that is positioned to face the support 303 and is used to jet out chemical precursor-containing gas uniformly onto the semiconductor wafer 301, and an outlet 320 to exhaust reaction gases and byproducts from the reaction chamber 302.

On one side of the reaction chamber 302, an opening 319 is formed and the reaction chamber is connected to a transfer chamber (not shown) to bring a semiconductor wafer or other substrate in and carry it out via a gate valve 318.

The support 303 that is provided within the reaction chamber 302 and is used to place the semiconductor wafer 301 is made of anodized aluminum or aluminum alloy and is grounded 327 to constitute one side of an electrode of plasma discharge. The reaction chamber 302 of the illustrated embodiment is thus a plasma CVD chamber configured for in situ (in chamber) plasma generation. Within the illustrated support 303, a ring-shape heating element 326 is embedded and the semiconductor wafer's temperature is controlled at a predetermined temperature using a temperature controller (not shown). The support 303 is connected to a driving mechanism 325 that moves the support 303 up and down through a support piston 329.

Within the reaction chamber 302, the showerhead 304 is provided at a position facing the support 303. In the showerhead 304, thousands of fine holes are provided to inject chemical precursor-containing gas onto the semiconductor wafer 301. The showerhead 304 is electrically connected to a high-frequency oscillator 308 via matching circuit 310 and constitutes another electrode of plasma discharge. Gas conduit 311 is used to bring chemical precursor-containing gas to showerhead 304 for film formation. The number of the gas conduit 311 is not limited to one. According to the type of chemical precursor, the necessary number of gas conduits can be installed. One end of the gas conduit 311 constitutes a gas inlet port 305 to cause gas to flow in and the other end constitutes a reaction gas exit port 307 to cause gas to flow out to the showerhead 304. The chemical precursor-containing and carrier gases can be stored and introduced to the inlet port(s) 305 by gas lines configured similarly to the gas line schematic shown in FIG. 2. Along the path of the reaction gas conduit 311, a mass flow controller (not shown) and valve 306 are positioned.

On the side wall of the reaction chamber 302, an outlet 320 is provided. The outlet 320 is connected to a vacuum exhaust pump (not shown) through piping 317. Between the outlet 320 and the vacuum pump, a conductance-controlling valve 321 is provided to regulate pressure within the reaction chamber 302. The conductance-controlling valve 321 is electrically connected to an external regulator 328.

Additionally, a pressure gauge 329 is preferably provided to measure pressure within the reaction chamber 302. This pressure gauge 329 is electrically connected to the regulator 328. An observation window 323 is preferably also provided on the side wall of the reaction chamber 302 and a charged coupled device (CCD) detector 322 is mounted on the observation window 323. Furthermore, a monitor 324 is installed on the CCD detector 322. The observation window 323 is preferably made of sapphire, but aluminum oxide can also be used. Also, in addition to the CCD detector, a photomultiplier tube or a photoelectric converter can also be used.

As mentioned above, the term "substrate" as used herein is a broad term that is used in its ordinary sense and includes not only the object e.g., wafer, placed into the CVD chamber to receive the film but also coated substrates, e.g., substrates onto which one or more films have already been applied. Examples of suitable substrates include silicon wafers and glass substrates.

A CVD process for depositing a Si-containing material on a surface is preferably conducted by introducing a gas to a CVD chamber as described herein, where the gas contains one or more reagents, preferably one or more chemical precursors. A chemical precursor is a reagent compound or mixture thereof that, upon contact with a heated substrate or exposure to a plasma, becomes chemically active and reacts with a material on the surface of the substrate or with another chemical precursor to create or modify a film on the surface of the substrate. Preferred chemical precursors are selected to form a film having a dielectric constant of about 3.5 or lower, preferably about 3.0 or lower, more preferably less than 3.0, even more preferably about 2.7 or lower, most preferably about 2.5 or lower, when deposited by the processes described herein. Preferred chemical precursors include a compound containing at least one silicon atom and at least one carbon atom, and a compound containing at least one carbon atom and at least one oxygen atom. The illustrated chemical precursors contain at least silicon atoms or carbon atoms, preferably both silicon and carbon atoms, more preferably all of silicon, carbon and oxygen atoms. Chemical precursors can be primary chemical precursors or secondary chemical precursors, and the gas preferably contains one or more primary chemical precursors and may optionally contain one or more secondary chemical precursors, as discussed elsewhere herein.

Depositing the film onto the substrate may be conducted by any suitable deposition process, preferably by thermal CVD. The term "thermal CVD" is used herein in its ordinary sense and means that the chemical precursors are activated by thermal energy, without additional plasma energy. Depositing the chemical precursor onto the substrate by thermal CVD can take place at a temperature that is lower than 300° C., but deposition rates tend to be higher at higher temperatures. Deposition by thermal CVD is preferably carried out at a temperature of about 300° C. or higher, more preferably about 350° C. or higher, most preferably about 400° C. or higher. Depositing can take place at a temperature in excess of 700° C., but deposition at lower temperatures is usually preferred in order to conserve thermal budgets. Deposition by thermal CVD is preferably carried out at a temperature of about 700° C. or lower, more preferably about 600° C. or lower, even more preferably about 550° C. or lower. Deposition is preferably accomplished by adjusting the temperature of the substrate to the desired deposition temperature by known methods such as heat lamps, ovens or resistive heaters. A preferred deposition temperature is in the range of about 350° C. to about 700° C., more preferably 400° C. to about 550° C., and is preferably accomplished by heating the substrate with radiant, convective and/or inductive heaters. The term "CVD," without qualifier, encompasses other chemical vapor deposition methods including "cold dissociation" methods that do not appreciably heat the precursors, such as plasma-enhanced and photon-assisted CVD. However, the chemical precursors disclosed herein are particularly advantageous for use in thermal CVD because they enable the practice of thermal CVD at relatively low temperatures. Thermal CVD is also preferred because it tends to be less complicated and less harmful than other CVD methods.

The deposition time can be varied as desired during the deposition process, either continuously or in steps. Depositing is preferably continued for a period of time that is effective to deposit a Si-containing film having the desired thickness. The term "film," as used herein, is a broad term and is used in its ordinary sense to encompass both single and multi-layer dielectric films. The desired thickness varies depending on the application, but preferably the film thickness is effective to electrically isolate conductive structures or features from each other within an integrated circuit. A preferred film thickness is in the range of from about 100 Å to about 10 m, more preferably about 1000 Å to about 1 m. Preferred deposition times can range from about 1 minute to about 120 minutes, more preferably from about 20 minutes to about 60 minutes, depending on the desired thickness, since film thickness is usually roughly proportional to deposition time.

The chemical precursor can be present in the gas in an amount that can vary over a broad range, depending on the depending on the nature of the particular precursor, the temperature, and the particular recipe used for deposition. Preferred amounts of chemical precursor in the gas can range from about 0.0001% to about 100%, more preferably about 0.0001% to about 75%, by volume based on total volume of gas. The gas can also contain reagents other than the chemical precursor, preferably carrier gases such as helium, hydrogen, argon, neon, krypton, or mixtures thereof. The flow rate of the gas and the relative proportions of each chemical precursor and carrier gas can vary over a broad range and may be selected for a particular application by varying the partial pressures of each in a routine manner to produce a film having the desired dielectric constant. Conventional equipment such as a bubbler can be used to aid in the introduction of any reagent that has relatively low volatility or that is not in the gaseous form at the storage temperature. Any chemical or carrier gas can be used in combination with one or more of any other chemical precursor or carrier gas to achieve the desired objective. A preferred film contains a desired balance of Si and C and, optionally, O and/or F, and thus preferably contains an amount of silicon in the range of about 1% to about 60%, more preferably about 5% to about 35%; an amount of carbon in the range of about 10% to about 90%, more preferably about 10% to about 50%; an amount of oxygen in the range of 0% to about 35%, more preferably about 1% to about 15%; and an amount of fluorine in the range of about 0% to about 67%, more preferably about 0% to about 65%; each by weight based on total.

Primary chemical precursors have one or more preferred features that facilitate the formation of a low-k film or that provide the resulting film with one or more desirable properties. Preferred primary chemical precursors include:

1. Siloxanes of the formula $(R_3Si)_2O$ where each R is independently H, D, F, methyl, ethyl or propyl, preferably in which at least one R is F, methyl or ethyl, more preferably $H_3SiOSiH_3$, $H_3CSiH_2OSiH_2CH_3$, and $F_3SiOSiF_3$. Siloxanes contain oxygen atoms and thus can be used without a separate source of oxygen. Preferred siloxanes such as $H_3SiOSiH_3$ and $F_3SiOSiF_3$ do not contain any C—H bonds, which tend to be more difficult to eliminate thermally at low reaction temperatures. Films resulting from siloxanes that contain fluorine atoms tend to have lower dielectric constants. Siloxanes are preferred precursors for thermal CVD at temperatures in the range of about 300° C. to about 700° C.

2. (Fluoroalkyl)fluorosiloxanes of the formula $[((R_f)_{3-x-y}R^1_xF_y)Si]_2O$ where $R_f$ is a perfluoromethyl, perfluoroethyl or perfluoropropyl group, $R^1$ is H or D, x is 0 or 1, y is 1 or 2, and x+y=1 or 2, preferably in which $R_f$ is trifluoromethyl, more preferably $F_3CSiF_2OSiF_2CF_3$. (Fluoroalkyl) fluorosiloxanes contain oxygen atoms and thus can be used without a separate source of oxygen. They also contain fluorine atoms which tend to result in films having lower dielectric constants. Preferred (fluoroalkyl)fluorosiloxanes do not contain any C—H bonds, which tend to be more difficult to eliminate thermally at low reaction temperatures. (Fluoroalkyl)fluorosiloxanes are preferred precursors for thermal CVD at temperatures in the range of about 300° C. to about 700° C.

3. (Fluoroalkyl)silanes of the formula $(R_f)_{4-a}SiR^1_a$ where $R_f$ is a perfluoromethyl, perfluoroethyl or perfluoropropyl group, $R^1$ is H or D, and a is 0, 1, 2, or 3, preferably in which $R_f$ is trifluoromethyl, more preferably $F_3CSiH_3$; (alkyl) fluorosilanes of the formula $R^2_{4-b}SiF_b$ where $R^2$ is methyl, ethyl or propyl, and b is 1, 2, or 3, preferably in which $R^2$ is methyl or ethyl, more preferably $CH_3SiF_3$ and $CH_3CH_2SiF_3$. (Fluoroalkyl)silanes do not contain oxygen atoms and thus can be used with a separate source of oxygen. They contain fluorine atoms which tend to result in films with a lower dielectric constant. Preferred (fluoroalkyl) silanes do not contain any C—H bonds, which tend to be more difficult to eliminate thermally at low reaction temperatures. (Fluoroalkyl)silanes are preferred precursors for thermal CVD at temperatures in the range of about 300° C. to about 700° C.

4. (Fluoroalkyl)fluorosilanes of the formula $(R_f)_{4-c-b}SiR^1_cF_b$ where $R_f$ is a perfluoromethyl, perfluorethyl or perfluoropropyl group, $R^1$ is H or D, c is 0, 1, or 2, b is 1, 2, or 3, and c+b=1, 2, or 3, preferably in which $R_f$ is trifluoromethyl, more preferably $F_3CSiF_3$. (Fluoroalkyl) fluorosilanes do not contain oxygen atoms and thus can be used with a separate source of oxygen. They contain relatively high levels of fluorine atoms which tend to result in films with a lower dielectric constant. Preferred (fluoroalkyl)silanes do not contain any C—H bonds, which tend to be more difficult to eliminate thermally at low reaction temperatures. (Fluoroalkyl)fluorosilanes are preferred precursors for thermal CVD at temperatures in the range of about 300° C. to about 700° C.

5. Alkylsiloxysilanes of the formula $(R_3SiO)_{4-b}SiR_b$ where each R is independently H, D, F, methyl, ethyl or propyl, and b is 1, 2 or 3, preferably in which each R is independently H, D, methyl or ethyl, more preferably $(CH_3)_3SiOSiH_3$. Alkylsiloxysilanes contain oxygen atoms and thus can be used without a separate source of oxygen. Alkylsiloxysilanes are sources of Si, C and O, and are preferred precursors for thermal CVD at temperatures in the range of about 300° C. to about 700° C.

6. Alkoxysilanes of the formula $(R^2O)_{4-a}SiR^1_a$ where $R^2$ is methyl, ethyl or propyl, $R^1$ is H or D, and a is 0, 1, 2, or 3, preferably in which $R^2$ is methyl or ethyl, more preferably $H_3COSiH_3$. Alkoxysilanes contain oxygen atoms and thus can be used without a separate source of oxygen. Alkoxysilanes are sources of Si, C and O, and are preferred precursors for thermal CVD at temperatures in the range of about 300° C. to about 700° C.

7. Alkylalkoxysilanes of the formula $(R^2O)_{4-c-b}SiR^2_bR^1_c$ where each $R^2$ is independently methyl, ethyl or propyl, $R^1$ is H or D, c is 0, 1, or 2, b is 1, 2, or 3, and c+b=1, 2, or 3, preferably in which $R^2$ is methyl or ethyl, more preferably $H_3COSiH_2CH_3$. Alkylalkoxysilanes contain oxygen atoms and thus can be used without a separate source of oxygen. Alkylalkoxysilanes are sources of Si, C and O, and are preferred precursors for thermal CVD at temperatures in the range of about 300° C. to about 700° C.

8. Silylmethanes of the formula $(H_3Si)_{4-a}CR^1_a$ where $R^1$ is H or D, and a is 0, 1, 2, or 3, more preferably $(H_3Si)_3CH$ and tetrasilylmethane, $(H_3Si)_4C$. Silylmethanes have a central carbon atom surrounded by one or more silyl groups and thus do not contain C—C bonds and contain no or relatively few C—H bonds, both of which tend to be difficult to eliminate thermally at low reaction temperature. The chemical properties of these molecules makes them very suitable for use as chemical precursors for the synthesis of "carbon-doped $SiO_2$" materials that have unique physical properties. This arises from the molecular structure of these molecules and their behavior during low temperature CVD. Use of these precursors favors the incorporation of carbon atoms into the resulting film that are bonded primarily to silicon atoms, thus decreasing the number of carbon-oxygen bonds. Silylmethanes do not contain oxygen atoms and thus can be used with a separate source of oxygen to deposit materials that contain oxygen. Silylmethanes are preferred precursors for thermal CVD at temperatures in the range of about 300° C. to about 700° C.

9. Alkoxysilylmethanes of the formula $(R^2O)_{4-c-b}(H_3Si)_bCR^1_c$ where $R^2$ is methyl, ethyl or propyl, $R^1$ is H or D, c is 0, 1, or 2, b is 1,2, or 3, and c+b=1,2, or 3, preferably in which $R^2$ is methyl or ethyl, more preferably $CH_3O(H_3Si)CH_2$. Alkoxysilylmethanes have a central carbon atom surrounded by one or more silyl groups and one or more alkoxy groups. They contain relatively few C—C and C—H bonds, both of which tend to be difficult to eliminate thermally at low reaction temperature. Alkoxysilylmethanes contain oxygen atoms and thus can be used without a separate source of oxygen. Alkoxysilylmethanes are preferred precursors for thermal CVD at temperatures in the range of about 300° C. to about 700° C.

10. Alkylalkoxysilylmethanes of the formula $(R^2O)_{4-x-y-z}R^2_z(H_3Si)_yCR^1_x$ where each $R^2$ is independently methyl, ethyl or propyl, $R^1$ is H or D, x is 0 or 1, y is 1 or 2, z is 1 or 2, and x+y+z=2 or 3, preferably in which each $R^2$ is independently methyl or ethyl, more preferably $(CH_3O)(CH_3)_2(H3Si)C$ and $(CH_3O)(CH_3)(H_3Si)_2C$. Alkylalkoxysilylmethanes have a central carbon atom surrounded by one or more silyl groups, one or more alkoxy groups, and one or more alkyl groups. They contain relatively few C—C and C—H bonds, both of which tend to be difficult to eliminate thermally at low reaction temperature. Alkylalkoxysilylmethanes contain oxygen atoms and thus can be used without a separate source of oxygen. Alkylalkoxysilylmethanes are preferred precursors for PECVD and for thermal CVD at temperatures in the range of about 200° C. to about 700° C.

11. Alkoxymethanes of the formula $(R^3O)_{4-a}CR^1{}_a$ where $R^3$ is methyl, ethyl, propyl, or t-butyl, $R^1$ is H or D, and a is 0, 1, 2, or 3, preferably $(CH_3O)_4C$ and $(CH_3O)_3CH$. Alkoxymethanes contain oxygen atoms and thus can be used without a separate source of oxygen. Alkoxymethanes are a source of carbon and oxygen, but do not contain silicon and thus are preferably used in combination with a silicon source. Alkoxymethanes are preferred precursors for thermal CVD at temperatures in the range of about 350° C. to about 600° C.

12. Alkylalkoxymethanes of the formula $(R^3O)_{4-c-b}R^2{}_bCR^1{}_c$ where $R^3$ is methyl, ethyl, propyl, or t-butyl, $R^2$ is methyl, ethyl or propyl, $R^1$ is H or D, c is 0, 1, or 2, b is 1, 2, or 3, and c+b=1, 2, or 3, preferably $(CH_3)(CH_3O)_3C$ and $(CH_3)(CH_3O)_2CH$. Alkylalkoxymethanes contain oxygen atoms and thus can be used without a separate source of oxygen. Alkylalkoxymethanes are a source of carbon and oxygen, but do not contain silicon and thus are preferably used in combination with a silicon source. Alkylalkoxymethanes are preferred precursors for PECVD and for thermal CVD at temperatures in the range of about 150° C. to about 700° C.

13. Mixtures of any two or more of the primary chemical precursors described herein. Preferably, mixtures are used when a particular single primary chemical precursor lacks the correct amount of a desired element. For instance, a second primary chemical precursor containing the desired element could be mixed with the other primary chemical precursor to produce a mixture having the desired balance of elements.

In addition to one or more primary chemical precursors, the gas can optionally contain one or more secondary chemical precursors. For instance, the gas preferably contains one or more secondary chemical precursors if the use of one or more of the aforementioned primary chemical precursors does not provide the desired balance of elements, the desired film structure, or the desired atom-to-atom bonding in the resulting film, e.g., the desired balance of Si, C and O. For example, when the gas contains a chemical precursor that does not contain silicon such as an alkoxymethane or an alkylalkoxymethane, it is preferable for the gas to also contain a secondary chemical precursor that is a silicon source. Likewise, when the gas contains a primary chemical precursor that does not contain oxygen, it is preferable for the gas to also contain a secondary chemical precursor that is an oxygen source. The secondary chemical precursor can also serve as a supplemental source of a desired element. For example, even when the primary precursor contains the desired element, the gas can further include a secondary chemical precursor that serves as a supplemental source of that element in order to further increase the relative amount of that element in the resulting film. Use of mixtures can also enable the deposition of thin film materials with tailored structures and controlled atom-to-atom connectivity. This represents an important advantage over spin-on techniques where the products that are to be spun-on have to be synthesized in solution through thermodynamically-governed equilibrium reactions, as opposed to CVD materials that can be synthesized using non-equilibrium, kinetically controlled reactions.

The desired balance of elements in the film can also be obtained by using a gas that is substantially free of a given chemical precursor. For instance, if a primary chemical precursor contains the desired element, it may be preferable for the secondary chemical precursor to not contain further amounts of that element. As an example, in a preferred embodiment a "single source" precursor is used that that contains an oxygen atom or atoms in its chemical structure, so that the gas need only contain minimal amounts of oxidizing agents, preferably about 1% or less, more preferably the gas does not contain an oxidizing agent. The absence of an oxidizing agent in the gas is preferred when the gas contains a primary chemical precursor that contains one or more oxygen atoms within its chemical structure. Oxidizing agents are compounds which have a strong oxidizing effect under CVD conditions and include compounds such as oxygen, ozone, hydrogen peroxide, nitrous oxide and water.

Preferred secondary chemical precursors can serve as a source of the element or elements that are desirable to incorporate into the film. Preferred secondary chemical precursors thus include silicon sources such as silane, disilane and trisilane, carbon sources such as methane, ethane, propane and butane, and oxygen sources such as oxygen, ozone, hydrogen peroxide, nitrous oxide and water. A secondary chemical precursor can be a source of two of more elements, e.g., chemical precursors such as methylsilane, dimethylsilane, trimethylsilane, tetramethylsilane, silylmethane, disilylmethane, trisilylmethane, and tetrasilylmethane can be a source of both silicon and carbon.

Chemical precursors may be purchased from commercial sources or synthesized by methods well-known to those skilled in the art. Alkoxysilylmethanes and alkylalkoxysilylmethanes are preferred primary chemical precursors and, in a preferred embodiment, processes for making them are provided. These processes preferably comprise reacting a halogenated precursor with a Si-containing reagent. In one such process, alkoxysilylmethanes of the formula $(R^2O)_{4-c-b}(H_3Si)_bCR^1{}_c$ where $R^2$ is methyl, ethyl or propyl, $R^1$ is H or D, c is 0, 1, or 2, b is 1, 2, or 3, and c+b=1, 2, or 3, are preferably synthesized by a metathesis reaction by reacting the corresponding halogenated alkoxymethane $(R^2O)_{4-c-b}X_bCR^1{}_c$ with a silyl salt $MSiH_3$, where X is a halogen selected from Cl, Br, and I, and M is a metal selected from Li, Na, K, and Cs, with K preferred. A specific example is the synthesis of dimethoxydislylmethane from dimethoxydichloromethane and potassium silyl:

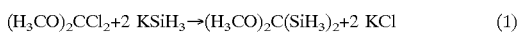

$$(H_3CO)_2CCl_2 + 2\ KSiH_3 \rightarrow (H_3CO)_2C(SiH_3)_2 + 2\ KCl \quad (1)$$

These reactions are preferably conducted by combining the reagents in an ether solvent cooled to −40° C. that is contained in a reaction vessel that is filled with pure, dry nitrogen and connected to an exhausted pressure relief bubbler. A typical reaction involves the dropwise addition of a solution of dimethoxydichloromethane in diethyl ether to a stoichiometric mixture of potassium silyl in diethyl ether that is stirred with a glass coated magnetic stir bar. Other suitable solvents include dibutyl ether, ethylene glycol dimethyl ether (glyme), diglyme and tetraglyme. During the addition of the dimethoxydichloromethane, the temperature of the mixture should be maintained at about −40° C. The mixture can then be allowed to slowly warm to room temperature with constant stirring. The crude disilyldimethoxymethane produced during the reaction can be isolated from the bulk of the solvent by vacuum distillation, using distillation techniques appropriate to the solvent employed (i.e. vacuum distillation, conventional distillation under a pure nitrogen atmosphere or reduced pressure distillation). The product can be characterized using Fourier-Transform infrared spectroscopy (FTIR), $^1$H NMR and $^{13}$C NMR. Appropriate safety precautions must be exercised for reactions involving potentially dangerous materials, e.g. pyrophoric gases such as silane or disilane.

In another such process, alkoxysilylmethanes of the formula $(R^2O)_{4-c-b}(H_3Si)_bCR^1_c$ where $R^2$ is methyl, ethyl or propyl, $R^1$ is H or D, c is 0, 1, or 2, b is 1, 2, or 3, and c+b=1, 2, or 3, are preferably synthesized by reacting the corresponding halogenated alkoxymethane $(R^2O)_{4-c-b}X_bCR^1_c$ with disilane $H_3SiSiH_3$, where X is a halogen selected from Cl, Br, and I. A specific example is the synthesis of methoxydisilylmethane from methoxydifluoromethane and disilane:

$$(H_3CO)CHF_2 + 2(H_3SiSiH_3) \rightarrow (H_3CO)CH(SiH_3)_2 + 2\ FSiH_3 \qquad (2)$$

These reactions are preferably conducted by combining the reagents in an ether solvent cooled to about −78° C. that is contained in a reaction vessel that is filled with pure, dry nitrogen and connected to an exhausted pressure relief bubbler. A typical reaction involves the dropwise addition of a solution of dimethoxydifluoromethane in diethyl ether to a stoichiometric soluition of disilane in diethyl ether that is stirred with a glass coated magnetic stir bar. Other suitable solvents include dibutyl ether, ethylene glycol dimethyl ether (glyme), diglyme and tetraglyme. During the addition of the dimethoxydifluoromethane, the temperature of the mixture should be maintained at about −78° C. The mixture can then be allowed to slowly warm to room temperature with constant stirring and then stirred for an additional 5 hours. The crude disilyldimethoxymethane produced during the reaction can be isolated from the bulk of the solvent using appropriate vacuum distillation techniques. All appropriate safety precautions must be exercised during the separation of the product from any unreacted disilane because it is a pyrophoric gas. Likewise, great care must be exercised in isolating the product from the fluorosilane byproduct because it is also a pyrophoric gas. The product can be purified using distillation techniques appropriate to the solvent employed (i.e. vacuum distillation, conventional distillation under a pure nitrogen atmosphere or reduced pressure distillation). The product can be characterized using Fourier-Transform infrared spectroscopy (FTIR), $^1$H NMR and $^{13}$C NMR. Appropriate safety precautions must be exercised for reactions involving potentially dangerous materials, e.g. pyrophoric gases such as fluorosilane or disilane.

In another such process, alkylalkoxysilylmethanes of the formula $(R^2O)_{4-x-y-z}R^2_z(H_3Si)_yCR^1_x$ where each $R^2$ is independently methyl, ethyl or propyl, $R^1$ is H or D, x is 0 or 1, y is 1 or 2, z is 1 or 2, and x+y+z=2 or 3, are preferably synthesized by a metathesis reaction by reacting the corresponding halogenated alkylalkoxymethane $(R^2O)_{4-x-y-z}R^2_zX_yCR^1_x$ with a silyl salt $MSiH_3$, where X is a halogen selected from Cl, Br, and I, and M is a metal selected from Li, Na, K, and Cs, with K preferred. A specific example is the synthesis of methyldimethoxysilylmethane from methyldimethoxychloromethane and potassium silyl:

$$(H_3C)(H_3CO)_2CCl + KSiH_3 \rightarrow (H_3C)(H_3CO)_2C(SiH_3) + KCl \qquad (3)$$

These reactions are preferably conducted by combining the reagents in an ether solvent cooled to about −40° C. that is contained in a reaction vessel that is filled with pure, dry nitrogen and connected to an exhausted pressure relief bubbler. A typical reaction involves the dropwise addition of a solution of dimethoxy(methyl)chloromethane in diethyl ether to a stoichiometric mixture of potassium silyl in diethyl ether that is stirred with a glass coated magnetic stir bar. Other suitable solvents include dibutyl ether, ethylene glycol dimethyl ether (glyme), diglyme and tetraglyme. During the addition of the dimethoxy(methyl)chloromethane, the temperature of the mixture should be maintained at about −40° C. The mixture can then be allowed to slowly warm to room temperature with constant stirring. The crude silyldimethoxy(methyl)methane produced during the reaction can be isolated from the bulk of the solvent using appropriate vacuum distillation techniques. The product can be purified using distillation techniques appropriate to the solvent employed (i.e. vacuum distillation, conventional distillation under a pure nitrogen atmosphere or reduced pressure distillation). The product can be characterized using Fourier-Transform infrared spectroscopy (FTIR), $^1$H NMR and $^{13}$C NMR. Appropriate safety precautions must be exercised for reactions involving potentially dangerous materials.

In another such process, alkylalkoxysilylmethanes of the formula $(R^2O)_{4-x-y-z}R^2_z(H_3Si)_yCR^1_x$ where each $R^2$ is independently methyl, ethyl or propyl, $R^1$ is H or D, x is 0 or 1, y is 1 or 2, z is 1 or 2, and x+y+z=2 or 3, are preferably synthesized by reacting the corresponding halogenated alkylalkoxymethane $(R^2O)_{4-x-y-z}R^2_zX_yCR^1_x$ with disilane $H_3SiSiH_3$, where X is a halogen selected from Cl, Br, and I. A specific example is the synthesis of methylmethoxysilylmethane from methylmethoxychloromethane and disilane:

$$(H_3C)(H_3CO)CHCl + H_3SiSiH_3 \rightarrow (H_3C)(H_3CO)CH(SiH_3) + ClSiH_3 \qquad (4)$$

These reactions are preferably conducted by combining the reagents in an ether solvent cooled to about −78° C. that is contained in a reaction vessel that is filled with pure, dry nitrogen and connected to an exhausted pressure relief bubbler. A typical reaction involves the dropwise addition of a solution of methoxy(methyl)chloromethane in diethyl ether to a stoichiometric soluition of disilane in diethyl ether that is stirred with a glass coated magnetic stir bar. Other suitable solvents include dibutyl ether, ethylene glycol dimethyl ether (glyme), diglyme and tetraglyme. During the addition of the methoxy(methyl)chloromethane, the temperature of the mixture should be maintained at about −78° C. The mixture can then be allowed to slowly warm to room temperature with constant stirring and then stirred for an additional 5 hours. The crude silylmethoxymethane produced during the reaction can be isolated from the bulk of the solvent using appropriate vacuum distillation techniques. All appropriate safety precautions must be exercised during the separation of the product from any unreacted disilane because it is a pyrophoric gas. Likewise, great care must be exercised in isolating the product from the chlorosilane byproduct because it is a pyrophoric gas. The product can be purified using distillation techniques appropriate to the solvent employed (i.e. vacuum distillation, conventional distillation under a pure nitrogen atmosphere or reduced pressure distillation). The product can be characterized using Fourier-Transform infrared spectroscopy (FTIR), $^1$H NMR and $^{13}$C NMR. Appropriate safety precautions must be exercised for reactions involving potentially dangerous materials, e.g. disilane and chlorosilane.

The Si-containing films that are deposited by the processes described herein preferably contain Si, C and O and preferably have a dielectric constant of about 3.5 or lower, more preferably about 3.0 or lower, even more preferably about 2.7 or lower, most preferably about 2.5 or lower. Dielectric constant is preferably determined on an "as deposited" basis. Further treatment of the as-deposited film may be conducted but, unlike spin-on processes, further treatment is generally not required in order to lower the dielectric constant or produce a thermally stable product.

In a preferred embodiment, a process is provided for making a multi-layered Si-containing film by depositing one or more additional layers onto a first Si-containing film. This embodiment provides a CVD chamber and a substrate, where the substrate is disposed within the chamber. A first gas comprised of a first chemical precursor, preferably a primary chemical precursor as described elsewhere herein, is introduced to the chamber, and a first Si-containing film is deposited onto the substrate. A second gas comprised of a second chemical precursor, preferably a primary chemical precursor as described elsewhere herein, is then introduced to the CVD chamber and a second film, preferably a Si-containing film, is deposited onto the first Si-containing film to form a multi-layered Si-containing film.

The deposition conditions for each layer of the multi-layer film are preferably within the ranges described elsewhere herein for the deposition of a Si-containing film. For any particular multi-layer film, the deposition conditions for the second film layer are preferably different from the deposition conditions used to deposit the first Si-containing film. For instance, two layers can be deposited sequentially by thermal CVD, the first layer using a first chemical precursor at a first temperature, and the second layer using a second chemical precursor at a second temperature. Alternatively, the first layer can be deposited by thermal CVD and the second layer by PECVD, or vice versa.

Preferably, the second chemical precursor is different from the first chemical precursor used to deposit the first Si-containing film. The second chemical precursor can be "different" from the first chemical precursor in various ways. For instance, the second chemical precursor is different from the first chemical precursor if it is a different chemical species e.g., if it has a different chemical structure. Also, since a chemical precursor can consist of a mixture of one or more chemical precursors, the second chemical precursor is different if it contains the same chemical precursors as the first chemical precursor but the relative amounts of each precursor within the mixture are not the same.

Each layer of the multi-layer film has an overall elemental composition. Preferably, the elemental composition of each layer is substantially different from that of any adjacent layer or layers in contact with it. In this context, the elemental composition of a layer is "substantially different" from an adjacent layer if the carbon, silicon, oxygen or fluorine content differs by 5% or more. For example, if a first layer contains 10% fluorine by weight based on total weight of the first layer, then an adjacent second layer that contains 20% fluorine by weight based on total weight of the second layer has an elemental composition that is substantially different from the first layer because the fluorine content differs by 10%.

Each layer of the multi-layer film has a dielectric constant. Preferably, the dielectric constant of each layer is substantially different from that of any adjacent layer or layers in contact with it. In this context, the dielectric constant of a layer is "substantially different" from an adjacent layer if the dielectric constant differs by 0.1 or more. For example, if a first layer has a dielectric constant of 3.0, then an adjacent second layer that has a dielectric constant of 2.8 is substantially different from the first layer because the dielectric constant value differs by 0.2.

Additional layers can be deposited in a similar manner to produce films having numerous layers, e.g. 3, 4, 5, or even 10 or more layers. For instance, in a preferred embodiment, a third gas comprised of a third chemical precursor, different from the second chemical precursor, is introduced to the chamber, and a third film is deposited on the second film to provide a multi-layered Si-containing film having at least three layers. Preferably, each layer of the multi-layer film individually has a dielectric constant of about 3.5 or lower, more preferably about 3.0 or lower, even more preferably about 2.7 or lower, most preferably about 2.5 or lower, as deposited. Preferably, each layer within the multi-layer film has a thickness in the range of about 50 Å to about 5000 Å, more preferably about 150 Å to about 2500 Å. In a preferred embodiment having three layers, the middle layer is the thickest of the three layers and has the lowest dielectric constant of the three layers. The two outer layers are thinner and have a higher dielectric constant, but exhibit better adhesion to other structures within the device, as compared to the middle layer. Preferably one or more of the individual layers of the multi-layer film is deposited by thermal CVD at a temperature of about 300° C. or higher, more preferably at a temperature in the range of about 350° C. to about 700° C., even more preferably at a temperature in the range of about 400° C. to about 550° C.

The multi-layered Si-containing film preferably has a dielectric constant of about 3.5 or lower, more preferably about 3.0 or lower, even more preferably about 2.7 or lower, most preferably about 2.5 or lower. Dielectric constant is preferably measured by the parallel plate capacitance-voltage method, at a measurement frequency of 1 MHz. The thickness of the multi-layered film can range from about 100 Å to 30,000 Å, more preferably from about 150 Å to about 20,000 Å, even more preferably from about 200 Å to about 10,000 Å. Thickness and refractive index are both preferably measured by optical techniques, preferably spectroscopic ellipsometry.

A multi-layered film having a graded interface between one or more layers can be made by continuous variation of a deposition parameter e.g., by continuously varying the partial pressure of the first gas from its maximum value to zero, while the partial pressure of the second gas is increased from zero to the value used to deposit the second film layer. Multi-layered films can be slightly more complicated to deposit than a corresponding single layer film, but multi-layered films can provide better performance characteristics that justify the additional effort. For instance, a fluorinated film may provide the desired low dielectric constant, but the presence of the fluorine in the film may reduce the adhesion of the film to the substrate onto which it is deposited and/or to any material that is subsequently deposited on the fluorinated film.

Figure 4:
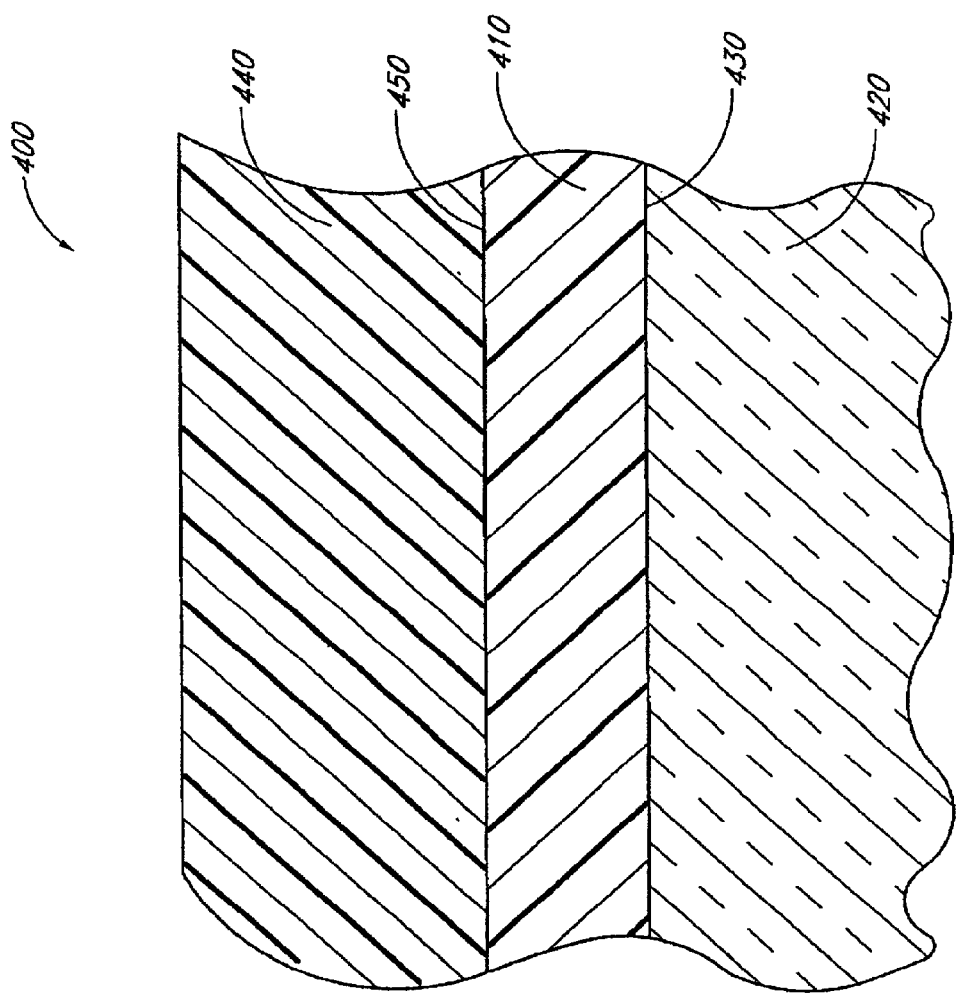
FIG. 4 is a schematic illustrating a multi-layered film having a graded interface in accordance with one embodiment of the invention.

Adhesion can be improved as illustrated in the multi-layer film 400 shown in FIG. 4 (not to scale) by depositing a first layer 410 onto the substrate 420 using a gas mixture that results in first layer 410 having an initial composition 430 in contact with substrate 420 that provides good adhesion to substrate 420, then varying the composition of the first gas until it matches the composition of the second gas that is used to subsequently deposit a fluorinated film 440. This variation in the gas composition causes the resulting first layer 410 to vary in composition from the initial composition 430, which preferably contains a relatively high level of silicon and a relatively low level of fluorine, to a more fluorinated composition 450. The first layer 410 thus provides adhesion between the fluorinated film 440 and the substrate 420 because it exhibits good adhesion to the substrate and the more highly fluorinated film. The improved adhesion to the fluorinated film arises from the elimination of a discrete interface between the two layers and a gradual change in elemental composition across the boundary region between the two films that promotes the formation of chemical bonds. The first layer 410 is preferably relatively thin, e.g., 50 Å, and the second fluorinated film 440 relatively thick, e.g. 2000 Å, so that the overall dielectric constant of the multi-layer film 400 is primarily controlled by the dielectric constant of fluorinated layer 440, not by the higher dielectric constant of first layer 410.

Preferably, for a multi-layer film comprised of two layers, the first layer is preferably comprised of an amount of silicon in the range of about 1% to about 60%, an amount of carbon in the range of about 10% to about 90%, an amount of oxygen in the range of 0% to about 35%, and an amount of fluorine in the range of 0% to about 67%, more preferably 0% to about 10%, each by weight based on total weight, and the second layer is comprised of an amount of silicon in the range of about 1% to about 50%, an amount of carbon in the range of about 10% to about 60%, an amount of oxygen in the range of 0% to about 30%, and an amount of fluorine in the range of 0% to about 67%, more preferably about 20% to about 65%, each by weight based on total weight. Preferably, the second layer has an elementary composition that is substantially different from the first layer.

For a multi-layer film comprised of three layers, the first two layers can be as set forth above for the multi-layer film comprised of two layers. Preferably, the third layer is comprised of an amount of silicon in the range of about 1% to about 60%, an amount of carbon in the range of about 10% to about 90%, an amount of oxygen in the range of 0% to about 35%, and an amount of fluorine in the range of 0% to about 65%. In a more preferred embodiment, the first layer is comprised of an amount of fluorine in the range of 0% to 10%, the second layer is comprised of an amount of fluorine in the range of about 20% to about 65%, and the third layer is comprised of an amount of fluorine in the range of 0% to about 10%, each by weight based on total weight. In another more preferred embodiment, the first layer is comprised of an amount of fluorine in the range of 0% to about 10%, the second layer is comprised of an amount of silicon in the range of about 10% to about 35%, and the third layer is comprised of an amount of fluorine in the range of 20% to about 65%, each by weight based on total weight. Preferably, the third layer has an elemental composition that is substantially different from the second layer.

Similar techniques can be used to impart other properties to the multi-layered low-k film, such as increased mechanical strength, thermal stability or resistance to diffusion e.g., diffusion of dopants. For instance, a multi-layered low-k film can be prepared by alternating relatively thick layers of a low-k material having relatively poor mechanical strength with relatively thin layers of a higher-k material having relatively high mechanical strength. Preferably, silylmethanes, alkoxysilylmethanes and siloxanes are used as chemical precursors to provide film layers having relatively high mechanical strength.

Preferred multi-layer films have 3 or more layers and each layer has a preferred range for silicon, carbon, oxygen and fluorine content as shown in Table 1 below for preferred multi-layer films A and B. Ranges of elemental percentage are expressed as a percentage by weight based on total weight. Percentages are approximate and need not add together to give 100% because the films may also contain other elements e.g. hydrogen. The percentages shown are intended to indicate the preferred ranges for each element.

TABLE 1

|  | % Si | % C | % O | % F |
| --- | --- | --- | --- | --- |
| Film A |  |  |  |  |
| Layer 1 | 10–90 | 10–70 | 5–35 | 0–1 |
| Layer 2 | 1–10 | 15–40 | 1–15 | 50–70 |
| Layer 3 | 10–90 | 10–70 | 5–35 | 0–1 |
| Film B |  |  |  |  |
| Layer 1 | 20–90 | 10–70 | 5–35 | 0–1 |
| Layer 2 | 10–70 | 10–70 | 5–35 | 0–1 |
| Layer 3 | 1–5 | 15–40 | 1–15 | 50–70 |
| Layer 4 | 10–35 | 10–70 | 5–35 | 0–1 |
| Layer 5 | 20–90 | 10–70 | 5–35 | 0–1 |

Each of the parameters in the processes described herein may be varied independently over a broad range and in any order in a manner that is effective to achieve the desired low-k film. For instance, one or more of the chemical precursors or carrier gases can be intermixed prior to introducing them to the chamber, e.g., in a pre-chamber, one or more of the chemical precursors or carrier gases can be introduced to the chamber separately, the deposition temperature can be varied in steps or continuously over the course of the process, and the partial pressure of each chemical precursor or carrier gas can be varied independently in steps or continuously over the course of the process.

The low-k films described herein can be incorporated into integrated circuits in the usual manner, particularly as inter-level dielectric layers between conductive levels (e.g., metal layers) within the circuit. The low-k films provide reduced parasitic capacitance and thus improved performance for the integrated circuits into which they are incorporated. Likewise, computer systems having improved performance may be obtained by incorporating the improved integrated circuits into the systems in the usual manner.

The processes described herein provide for the deposition of films with a broad range of elemental composition, and as a result, a broad range of physical properties. The number of layers, the thickness of each layer, the elemental composition of each layer and the atom-to-atom connectivity of each layer can all be controlled variables that allow for the synthesis of a broad range of controllable physical properties. This enables the CVD synthesis of a wide range of low-k dielectric materials that will have dielectric constants much less than that of silicon dioxide. Improved integration with other process steps within the semiconductor manufacturing process may also be achieved.

EXAMPLES

Dielectric constant in the following examples is measured by the parallel plate capacitance voltage method. Film thickness and refractive index are both measured simultaneously by spectroscopic ellipsometry.

Example 1

A Si-containing film having a low dielectric constant is deposited onto a substrate using thermal CVD as follows: A Si(100) wafer is introduced into the reactor chamber of an Eagle 10™ reactor system where it is placed upon a resistively heated susceptor. The temperature of the wafer is increased, under a flow of 10 SLM (standard liter per minute) nitrogen and a reactor pressure of 30 Torr, until it is stabilized at 500° C., as measured via a thermocouple contact within the susceptor block. A film comprised of silicon, carbon, hydrogen and oxygen is then deposited using disiloxane, $(H_3Si)_2O$ and dimethoxydimethylsilane, $(H_3CO)_2Si(CH_3)_2$, as the precursors. This is accomplished by introducing 30 SCCM (standard cubic centimeter per minute) disiloxane gas and 300 SCCM dimethoxy(dimethyl) silane, diluted in a flow of 10 SLM nitrogen carrier gas into the reactor chamber and exposing it to the heated Si(100) substrate surface at a reactor pressure of 30 Torr. The gas is introduced into the reactor chamber for a total of 20 minutes to deposit a film having approximate composition $Si_{12}C_{24}O_{12}H_{52}$ and a total thickness of about 10,000 Å onto the Si(100) substrate. The dielectric constant of the film is 2.7.

Example 2

A multi-layer Si-containing film having a low dielectric constant is deposited onto a substrate using thermal CVD as follows: A Si(100) wafer is introduced into the reactor chamber of an Eagle 10™ reactor system where it is placed upon a resistively heated susceptor. The temperature of the wafer is increased, under a flow of 10 SLM nitrogen and a reactor pressure of 30 Torr, until it is stabilized at 450° C., as via a thermocouple contact within the susceptor block. A first film comprised of silicon, carbon, and hydrogen is then deposited using disilylmethane, $(H_3Si)_2CH_2$, by introducing a flow of 50 SCCM of disilylmethane diluted in 10 SLM argon into the reactor at a pressure of 20 Torr. The deposition is conducted for 0.5 minute to deposit a film of approximate composition $Si_{40}C_{20}H_{40}$ having a thickness of 80 Å and a dielectric constant of 3.9. The disilylmethane flow is then terminated and the reactor chamber is purged using 10 SLM nitrogen at a chamber pressure of 20 Torr for 10 s. A second film comprised of silicon, carbon, hydrogen and oxygen is then deposited onto the first film using disiloxane, $(H_3Si)_2O$ and dimethoxysilane, $(H_3CO)_2SiH_2$, as the precursors. This is accomplished by introducing 10 SCCM disiloxane gas and 200 SCCM dimethoxysilane, diluted in a flow of 10 SLM argon carrier gas into the reactor chamber and exposing it to the heated substrate surface (first film) at a reactor pressure of 20 Torr. The gas is introduced into the reactor chamber for a total of 20 minutes to deposit a second film having approximate composition $Si_{13}C_{35}O_{11}H_{41}$ and a total thickness of 10,000 Å onto the first film. The dielectric constant of the second film is 2.6. The disiloxane and dimethoxysilane flows are then terminated and the reactor chamber is purged using 10 SLM nitrogen at a chamber pressure of 20 Torr for 10 seconds. A third film is then deposited in a manner identical to the first film to deposit 80 Å of a film having the approximate composition $Si_{40}C_{20}H_{40}$ onto the second film, the third film having a dielectric constant of 3.9. The dielectric constant of the total filmstack is 2.63.

Example 3

A multi-layer Si-containing film having a graded interface between layers and a low dielectric constant is deposited onto a substrate using thermal CVD as follows: A Si(100) wafer is introduced into the reactor chamber of an Eagle 10™ reactor system where it is placed upon a resistively heated susceptor. The temperature of the wafer is increased, under a flow of 10 SLM nitrogen and a reactor pressure of 20 Torr, until it is stabilized at 550° C., as measured via a thermocouple contact within the susceptor block. A first film comprised of silicon, carbon, and hydrogen is then deposited using disilylmethane, $(H_3Si)_2CH_2$, by introducing a flow of 50 SCCM of disilylmethane diluted in 10 SLM argon into the reactor at a pressure of 20 Torr. The deposition is conducted for 0.5 minute to deposit a film of approximate composition $Si_{40}C_{20}H_{40}$ having a thickness of 80 Å and a dielectric constant of 3.9. The disilylmethane flow is then ramped from 50 SCCM to 0 SCCM over a period of 10 seconds, while a flow of disiloxane is ramped from 0 SCCM to 20 SCCM and a flow of 1,2-bis-trifluoromethyldisiloxane, $((CF_3)_2HSi)_2O$ is ramped from 0 SCCM to 50 SCCM. At the end of 10 seconds, the disiloxane flow is terminated, while the 1,2-bis-trifluoromethyldisiloxane is ramped further to 200 SCCM over a period of 20 seconds. This ramping of the flow rates results in a graded composition film structure between the first layer and the next layer to be deposited, thereby eliminating a discrete interface between the two layers. A second film comprised of silicon, carbon, fluorine and oxygen is then deposited using the 200 SCCM flow of 1,2-bis-trifluoromethyldisiloxane as the precursor. This gas is introduced into the reactor chamber for a total of 10 minutes to deposit a film having composition $Si_{10}C_{21}O_5F_{64}$ and a total thickness of 10,000 Å onto the graded composition film. The dielectric constant is 2.4.

Example 4

A Si(100) wafer is introduced into the reactor chamber of an Eagle 10™ reactor system where it is placed upon a resistively heated susceptor. The temperature of the wafer is increased, under a flow of 10 SLM nitrogen and a reactor pressure of 20 Torr, until it is stabilized at 550° C., as measured via a thermocouple contact within the susceptor block. A first film comprised of silicon, carbon, and hydrogen is then deposited using disilylmethane, $(H_3Si)_2CH_2$, by introducing a flow of 50 SCCM of disilylmethane diluted in 10 SLM argon into the reactor at a pressure of 20 Torr. The deposition is conducted for 0.5 min to deposit a film of approximate composition $Si_{40}C_{20}H_{40}$ having a thickness of 80 Å and a dielectric constant of 3.9. The disilylmethane flow is then ramped from 50 SCCM to 0 SCCM over a period of 10 seconds, while a flow of disiloxane is ramped from 0 SCCM to 20 SCCM and a flow of 1,2-bis-trifluoromethyldisiloxane, $((CF_3)_2HSi)_2O$ is ramped from 0 SCCM to 50 SCCM. At the end of 10 seconds, the disiloxane flow is terminated, while the 1,2-bis-trifluoromethyldisiloxane is ramped further to 200 SCCM over a period of 20 seconds. This ramping of the flow rates results in a graded composition film structure between the first layer and the next layer to be deposited, thereby eliminating a discrete interface between the two layers. A second film comprised of silicon, carbon, fluorine and oxygen is then deposited using the 200 SCCM flow of 1,2-bis-trifluoromethyldisiloxane as the precursor. This gas is introduced into the reactor chamber for a total of 10 minutes, after which time a film having composition $Si_{10}C_{21}O_5F_{64}$ and a total thickness of 10,000 Å, is deposited onto the graded composition film. The dielectric constant is 2.4. The flow rate of the 1,2-bis-trifluoromethyldisiloxane is then ramped to 50 SCCM over a period of 10 seconds, after which time a flow of 20 SCCM of disiloxane and 50 SCCM of disilylmethane are introduced into the reactor chamber. The flows of disiloxane and 1,2-bis-trifluoromethyldisiloxane are both ramped to 0 SCCM over a period of 10 seconds, while the flow of disilylmethane is kept at 50 SCCM. The disilylmethane is then used to deposit a film having approximate composition $Si_{40}C_{20}H_{40}$ to a thickness of 80 Å by flowing it for an additional 0.5 minute. The dielectric constant of the total filmstack is 2.45.

Example 5

The following reaction involves dangerous materials and should only be conducted on a small scale by trained individuals using appropriate safety precautions. A sample of dimethoxysilylmethane (I), $(H_3CO)_2(H_3Si)CH$, is prepared by reacting potassium silyl, $KSiH_3$ with dimethoxy (chloro)methane, $(H_3CO)_2CCl(H)$, as follows: A solution of $(H_3CO)_2CCl(H)$ (1.5 g, 13.6 mmol) in 30 ml diethyl ether is added dropwise, with constant stirring, to a mixture of $KSiH_3$ (1.0 g, 14.2 mmol) and 100 ml diethyl ether cooled to $-40°$ C. over thirty minutes. The resulting mixture is allowed to warm slowly to room temperature and stirred for an additional 5 hours. The bulk of the solvent is removed in vacuo by passing the volatiles through traps maintained at $-40°$ C. and $-196°$ C. Crude (I) is collected in the $-40°$ C. trap as a colorless mobile liquid. The crude product is further purified via distillation under pure, dry nitrogen to yield pure (I). The compound is characterized by FTIR, $^1H$ NMR and $^{13}C$ NMR, elemental analysis and GC-MS.

Example 6

The following reaction involves dangerous materials and should only be conducted on a small scale by trained individuals using appropriate safety precautions. Methoxy (methyl)silylmethane (II), $(H_3CO)(H_3C)(H_3Si)CH$, is prepared by reacting potassium silyl, $KSiH_3$ and methoxymethyl(chloro)methane, $(H_3CO)(H_3C)CCl(H)$ as follows: A solution of $(H_3CO)(H_3C)CCl(H)$ (1.8 g, 19.0 mmol) in 30 ml diethyl ether is added dropwise, with constant stirring, to a mixture of $KSiH_3$ (1.34 g, 19.1 mmol) and 100 ml diethyl ether cooled to $-40°$ C. over thirty minutes. The resulting mixture is allowed to warm slowly to room temperature and stirred for an additional 5 hours. The bulk of the solvent is removed in vacuo by passing the volatiles through traps maintained at $-40°$ C. and $-196°$ C. Crude (II) is collected in the $-40°$ C. trap as a colorless mobile liquid. The crude product is further purified via distillation under pure, dry nitrogen to yield pure (II). The compound is characterized through FTIR, $^1H$ NMR and $^{13}C$ NMR, elemental analysis and GC-MS.

Although the foregoing invention has been described in terms of certain preferred embodiments, other embodiments will become apparent to those of ordinary skill in the art in view of the disclosure herein. Accordingly, the present invention is not intended to be limited by the recitation of preferred embodiments, but is intended to be defined solely by reference to the appended claims.

I claim:

1. A thermal chemical vapor deposition process for depositing a Si-containing material on a surface, comprising
   providing a chemical vapor deposition chamber having disposed therein a substrate,
   introducing a gas to said chamber, wherein said gas is comprised of a chemical precursor,
   depositing a Si-containing film onto said substrate by thermal chemical vapor deposition, wherein said Si-containing film has a dielectric constant of less than 3.0, as deposited, and
   wherein said chemical precursor is selected from the group consisting of
   siloxanes of the formula $(R_3Si)_2O$ where each R is independently H, D, F, methyl, ethyl or propyl,
   (fluoroalkyl)fluorosiloxanes of the formula $[((R_f)_{3-x-y}R^1_xF_y)Si]_2O$ where $R_f$ is a perfluoromethyl, perfluoroethyl or perfluoropropyl group, $R^1$ is H or D, x is 0 or 1, y is 1 or 2, x+y=1 or 2,
   (fluoroalkyl)silanes of the formula $(R_f)_{4-a}SiR^1_a$ where $R_f$ is a perfluoromethyl, perfluoroethyl or perfluoropropyl group, $R^1$ is H or D, and a is 0, 1, 2, or 3,
   (alkyl)fluorosilanes of the formula $R^2_{4-b}SiF_b$ where $R^2$ is methyl, ethyl or propyl, and b is 1, 2, or 3,
   (fluoroalkyl)fluorosilanes of the formula $(R_f)_{4-c-b}SiR^1_cF_b$ where $R_f$ is a perfluoromethyl, perfluorethyl or perfluoropropyl group, $R^1$ is H or D, c is 0, 1, or 2, b is 1, 2, or 3, and c+b=1, 2, or 3,
   alkysiloxysilanes of the formula $(R_3SiO)_{4-b}SiR_b$ where each R is independently H, D, F, methyl, ethyl or propyl, and b is 1, 2 or 3,
   alkoxysilanes of the formula $(R^2O)_{4-a}SiR^1_a$ where $R^2$ is methyl, ethyl or propyl, $R^1$ is H or D, and a is 0, 1, 2, or 3,
   alkylalkoxysilanes of the formula $(R^2O)_{4-c-b}SiR^2_bR^1_c$ where each $R^2$ is independently methyl, ethyl or propyl, $R^1$ is H or D, c is 0, 1, or 2, b is 1, 2, or 3, and c+b=1, 2, or 3,
   silylmethanes of the formula $(H_3Si)_{4-a}CR^1_a$ where $R^1$ is H or D, and a is 0, 1, 2, or 3,
   alkoxysilylmethanes of the formula $(R^2O)_{4-c-b}(H_3Si)_bCR^1_c$ where $R^2$ is methyl, ethyl or propyl, $R^1$ is H or D, c is 0, 1, or 2, b is 1, 2, or 3, and c+b=1, 2, or 3,
   alkylalkoxysilylmethanes of the formula $(R^2O)_{4-x-y-z}R^2_z(H_3Si)_yCR^1_x$ where each $R^2$ is independently methyl, ethyl or propyl, $R^1$ is H or D, x is 0 or 1, y is 1 or 2, z is 1 or 2, and x+y+z=2 or 3,
   alkoxymethanes of the formula $(R^3O)_{4-a}CR^1_b$ where $R^3$ is methyl, ethyl, propyl, or t-butyl, $R^1$ is H or D, and a is 0, 1, 2, or 3,
   alkylalkoxymethanes of the formula $(R^3O)_{4-c-b}R^2_bCR^1_c$ where $R^3$ is methyl, ethyl, propyl, or t-butyl, $R^2$ is methyl, ethyl or propyl, $R^1$ H or D, c is 0, 1, or 2, b is 1, 2, or 3, and c+b=1, 2, or 3,
   and mixtures thereof.

2. The thermal chemical vapor deposition process of claim 1 wherein said Si-containing film is deposited onto said substrate at a temperature greater than about 300° C.

3. The thermal chemical vapor deposition process of claim 1 wherein said Si-containing film is deposited onto said substrate at a temperature in the range of about 350° C. to about 700° C.

4. The thermal chemical vapor deposition process of claim 1 wherein said Si-containing film is deposited onto said substrate at a temperature in the range of about 400° C. to about 550° C.

5. The thermal chemical vapor deposition process of claim 1 wherein said Si-containing film has a dielectric constant of about 2.7 or lower.

6. The thermal chemical vapor deposition process of claim 1 wherein said Si-containing film has a dielectric constant of about 2.5 or lower.

7. The thermal chemical vapor deposition process of claim 1 wherein said gas does not contain an oxidizing agent.

8. The thermal chemical vapor deposition process of claim 1 wherein said chemical precursor is selected from the group consisting of
   a siloxane of the formula $(H_3Si)_2O$,
   a siloxane of the formula $(R_3Si)_2O$ in which at least one R is F,
   a siloxane of the formula $(R_3Si)_2O$ in which at least one R is methyl or ethyl,
   a (fluoroalkyl)fluorosiloxane of the formula $[((R_f)_{3-x-y}R^1_xF_y)Si]_2O$ in which $R_f$ is trifluoromethyl, a (fluoroalkyl)silane of the formula $(R_f)_{4-a}SiR^1_a$ in which $R_f$ is trifluoromethyl, an (alkyl)fluorosilane of the formula $R^2_{4-b}SiF_b$ in which $R^2$ is methyl or ethyl, a (fluoroalkyl)fluorosilane of the formula $(R_f)_{4-c-b}SiR^1_cF_b$ in which $R_f$ is trifluoromethyl, an alkylsiloxysilane of the formula $(R_3SiO)_{4-b}SiR_b$ in which each R is independently H, D, methyl, or ethyl, an alkoxysilane of the formula $(R^2O)_{4-a}SiR^1_a$ in which $R^2$ is methyl or ethyl, an alkylalkoxysilane of the formula $(R^2O)_{4-c-b}SiR^2_bR^1_c$ in which each $R^2$ is independently methyl or ethyl, an alkoxysilylmethane of the formula $(R^2O)_{4-c-b}(H_3Si)_b CR^1_c$ in which $R^2$ is methyl or ethyl, and an alkylalkoxysilylmethane of the formula $(R^2O)_{4-x-y-z}R^2_x(H_3Si)_yCR^1_z$ in which each $R^2$ is independently methyl or ethyl.

9. A thermal chemical vapor deposition process for depositing a Si-containing material on a surface, comprising providing a chemical vapor deposition chamber having disposed therein a substrate, introducing a gas to said chamber, wherein said gas is comprised of a first chemical precursor selected from the group consisting of siloxanes of the formula $(R_3Si)_2O$ where each R is independently H, D, F, methyl, ethyl or propyl, (fluoroalkyl)fluorosiloxanes of the formula $[((R_f)_{3-x-y}R^1_xF_y)Si]_2O$ where $R_f$ is a perfluoromethyl, perfluoroethyl or perfluoropropyl group, $R^1$ is H or D, x is 0 or 1, y is 1 or 2, and x+y=1 or 2, (fluoroalkyl)silanes of the formula $(R_f)_{4-a}SiR^1_a$ where $R_f$ is a perfluoromethyl, perfluoroethyl or perfluoropropyl group, $R^1$ is H or D, and a is 0, 1, 2, or 3, (alkyl)fluorosilanes of the formula $R^2_{4-b}SiF_b$ where $R^2$ is methyl, ethyl or propyl, and b is 1, 2, or 3, (fluoroalkyl)fluorosilanes of the formula $(R_f)_{4-c-b}SiR^1_cF_b$ where $R_f$ is a perfluoromethyl, perfluorethyl or perfluoropropyl group, $R^1$ is H or D, c is 0, 1, or 2, b is 1, 2, or 3, and c+b=1, 2, or 3, alkylsiloxysilanes of the formula $(R_3SiO)_{4-b}SiR_b$ where each R is independently H, D, F, methyl, ethyl or propyl, and b is 1, 2 or 3, alkoxysilanes of the formula $(R^2O)_{4-a}SiR^1_a$ where $R^2$ is methyl, ethyl or propyl, $R^1$ is H or D, and a is 0, 1, 2, or 3, alkylalkoxysilanes of the formula $(R^2O)_{4-c-b}SiR^2_bR^1_c$ where each $R^2$ is independently methyl, ethyl or propyl, $R^1$ is H or D, c is 0, 1, or 2, b is 1, 2, or 3, and c+b=1, 2, or 3, silylmethanes of the formula $(H_3Si)_{4-a}CR^1_a$ where $R^1$ is H or D, and a is 0, 1, 2, or 3, alkoxysilylmethanes of the formula $(R^2O)_{4-c-b}(H_3Si)_b CR^1_c$ where $R^2$ is methyl, ethyl or propyl, $R^1$ is H or D, c is 0, 1, or 2, b is 1, 2, or 3, and c+b=1, 2, or 3, alkylalkoxysilylmethanes of the formula $(R^2O)_{4-x-y-z}R^2_z(H_3Si)_yCR^1_x$ where each $R^2$ is independently methyl, ethyl or propyl, $R^1$ is H or D, x is 0 or 1, y is 1 or 2, z is 1 or 2, and x+y+z=2 or 3, alkoxymethanes of the formula $(R^3O)_{4-a}CR^1_a$ where $R^3$ is methyl, ethyl, propyl, or t-butyl, $R^1$ is H or D, and a is 0, 1, 2, or 3, alkylalkoxymethanes of the formula $(R^3O)_{4-c-b}R^2_bCR^1_c$ where $R^3$ is methyl, ethyl, propyl, or t-butyl, $R^2$ is methyl, ethyl or propyl, $R^1$ is H or D, c is 0, 1, or 2, b is 1, 2, or 3, and c+b=1, 2, or 3, and mixtures thereof;

and depositing a Si-containing film onto said substrate by thermal chemical vapor deposition at a temperature of about 300° C. or higher, wherein said Si-containing film has a dielectric constant of about 3.5 or lower, as deposited.

10. The thermal chemical vapor deposition process of claim 9 wherein said first chemical precursor is selected from the group consisting of a siloxane of the formula $(H_3Si)_2O$, a siloxane of the formula $(R_3Si)_2O$ in which at least one R is F, a siloxane of the formula $(R_3Si)_2O$ in which at least one R is methyl or ethyl, a (fluoroalkyl)fluorosiloxane of the formula $[((R_f)_{3-x-y}R^1_xF_y)Si]_2O$ in which $R_f$ is trifluoromethyl, a (fluoroalkyl)silane of the formula $(R_f)_{4-a}SiR^1_a$ in which $R_f$ is trifluoromethyl, an (alkyl)fluorosilane of the formula $R^2_{4-b}SiF_b$ in which $R^2$ is methyl or ethyl, a (fluoroalkyl)fluorosilane of the formula $(R_f)_{4-c-b}SiR^1_cF_b$ in which $R_f$ is trifluoromethyl, an alkylsiloxysilane of the formula $(R_3SiO)_{4-b}SiR_b$ in which each R is independently H, D, methyl, or ethyl, an alkoxysilane of the formula $(R^2O)_{4-a}SiR^1_a$ in which $R^2$ is methyl or ethyl, an alkylalkoxysilane of the formula $(R^2O)_{4-c-b}SiR^2_bR^1_c$ in which each $R^2$ is independently methyl or ethyl, an alkoxysilylmethane of the formula $(R^2O)_{4-c-b}(H_3Si)_b CR^1_c$ in which $R^2$ is methyl or ethyl, and an alkylalkoxysilylmethane of the formula $(R^2O)_{4-x-y-z}R^2_z(H_3Si)_yCR^1_x$ in which each $R^2$ is independently methyl or ethyl.

11. The thermal chemical vapor deposition process of claim 9 wherein said gas is futher comprised of a second chemical precursor selected from the group consisting of silane, disilane, trisilane, methane, ethane, propane, butane, oxygen, ozone, hydrogen peroxide, nitrous oxide and water.

12. The thermal chemical vapor deposition process of claim 9 wherein said temperature is in the range of about 350° C. to about 700° C.

13. The thermal chemical vapor deposition process of claim 9 wherein said temperature is in the range of about 400° C. to about 550° C.

14. The thermal chemical vapor deposition process of claim 9 wherein said Si-containing film has a dielectric constant of about 3.0 or lower.

15. The thermal chemical vapor deposition process of claim 9 wherein said Si-containing film has a dielectric constant of about 2.7 or lower.

16. The thermal chemical vapor deposition process of claim 9 wherein said Si-containing film has a dielectric constant of about 2.5 or lower.

17. A chemical vapor deposition process for depositing a Si-containing material on a surface, comprising providing a chemical vapor deposition chamber having disposed therein a substrate;

introducing a gas to said chamber, wherein said gas is comprised of a first chemical precursor selected from the group consisting of silylmethanes of the formula $(H_3Si)_{4-a}CR^1_a$ where $R^1$ is H or D, and a is 0, 1, 2, or 3, alkoxysilylmethanes of the formula $(R^2O)_{4-c-b}(H_3Si)_b CR^1_c$ where $R^2$ is methyl, ethyl or propyl, $R^1$ is H or D, c is 0, 1, or 2, b is 1, 2, or 3, and c+b=1, 2 or 3 alkylalkoxysilylmethanes of the formula $(R^2O)_{4-x-y-z}R^2_z(H_3Si)_yCR^1_x$ where each $R^2$ is independently methyl, ethyl or propyl, $R^1$ is H or D, x is 0 or 1, y is 1 or 2, z is 1 or 2, and x+y+z=2 or 3, alkoxymethanes of the formula $(R^3O)_{4-a}CR^1_a$ where $R^3$ is methyl, ethyl, propyl, or t-butyl, $R^1$ is H or D, and a is 0, 1, 2, or 3, alkylalkoxymethanes of the formula $(R^3O)_{4-c-b}R^2_bCR^1_c$ where $R^3$ is methyl, ethyl, propyl, or t-butyl, $R^2$ is methyl, ethyl or propyl, $R^1$ is H or D, c is 0, 1, or 2, b is 1, 2, or 3, and c+b=1, 2, or 3, and mixtures thereof, and depositing a Si-containing film onto said substrate, wherein said Si-containing film has a dielectric constant of about 3.5 or lower, as deposited.

18. The chemical vapor deposition process of claim 17 wherein said Si-containing film is deposited by thermal chemical vapor deposition at a temperature of about 300° C. or higher.

19. The chemical vapor deposition process of claim 18 wherein said temperature is in the range of about 350° C. to about 700° C.

20. The chemical vapor deposition process of claim 18 wherein said temperature is in the range of about 400° C. to about 550° C.

21. The chemical vapor deposition process of claim 17 wherein said first chemical precursor is selected from to group consisting of an alkoxysilylmethane of the formula $(R^2O)_{4-c-b}(H_3Si)_b CR^1_c$ in which $R^2$ is methyl or ethyl, and an alkylalkoxysilylmethane of the formula $(R^2O)_{4-x-y-z}R^2_x(H_3Si)_yCR^1_x$ in which each $R^2$ is independently methyl or ethyl.

22. The chemical vapor deposition process of claim 17 wherein said first chemical precursor is tetrasilylmethane.

23. The chemical vapor deposition process of claim 17 wherein said gas is further comprised of a second chemical precursor selected from the group consisting of silane, disilane, trisilane, methane, ethane, propane, butane, oxygen, ozone, hydrogen peroxide, nitrous oxide and water.

24. The thermal chemical vapor deposition process of claim 17 wherein said Si-containing film has a dielectric constant of about 3.0 or lower.

25. The chemical vapor deposition process of claim 17 wherein said Si-containing film has a dielectric constant of about 2.7 or lower.

26. The chemical vapor deposition process of claim 17 wherein said Si-containing film has a dielectric constant of about 2.5 or lower.

27. A chemical vapor deposition process for depositing a Si-containing material on a surface, comprising providing a chemical vapor deposition chamber having disposed therein a substrate;

introducing a first gas to said chamber, wherein said first gas is comprised of a first chemical precursor, depositing a first Si-containing film onto said substrate, wherein said first Si-containing film has a dielectric constant of about 3.5 or lower, as deposited, and wherein said first Si-containing film has a thickness in the range of about 50 Å to about 5000 Å, introducing a second gas to said chamber, wherein said second gas is comprised of a second chemical precursor different from said first chemical precursor, and depositing a second Si-containing film onto said first Si-containing film to provide a multi-layered Si-containing film, wherein said second Si-containing film has a dielectric constant of about 3.5 or lower, as deposited, wherein said second Si-containing film has a thickness in the range of about 50 Å to about 5000 Å, and wherein said multi-layered Si-containing film has a dielectric constant of about 3.5 or lower, as deposited.

28. The chemical vapor deposition process of claim 27 wherein said multi-layered Si-containing film has a dielectric constant of about 3.0 or lower.

29. The chemical vapor deposition process of claim 27 wherein said multi-layered Si-containing film has a dielectric constant of about 2.7 or lower.

30. The chemical vapor deposition process of claim 27 wherein said multi-layered Si-containing film has a dielectric constant of about 2.5 or lower.

31. The chemical vapor deposition process of claim 27 wherein said first Si-containing film is deposited by thermal chemical vapor deposition at a temperature of about 300° C. or higher.

32. The chemical vapor deposition process of claim 31 wherein said temperature is in the range of about 350° C. to about 700° C.

33. The chemical vapor deposition process of claim 31 wherein said temperature is in the range of about 400° C. to about 550° C.

34. The chemical vapor deposition process of claim 27 wherein said first chemical precursor is selected from the group consisting of siloxanes of the formula $(R_3Si)_2O$ where each R is independently H, D, F, methyl, ethyl or propyl, (fluoroalkyl)fluorosiloxanes of the formula $[((R_f)_{3-x-y}R^1_xF_y)Si]_2O$ where $R_f$ is a perfluoromethyl, perfluoroethyl or perfluoropropyl group, $R^1$ is H or D, x is 0 or 1, y is 1 or 2, and x+y=1 or 2, (fluoroalkyl)silanes of the formula $(R_f)_{4-a}SiR^1_a$ where $R_f$ is a perfluoromethyl, perfluoroethyl or perfluoropropyl group, $R^1$ is H or D, and a is 0, 1, 2, or 3, (alkyl)fluorosilanes of the formula $R^2_{4-b}SiF_b$ where $R^2$ is methyl, ethyl or propyl, and b is 1, 2, or 3, (fluoroalkyl)fluorosilanes of the formula $(R_f)_{4-c-b}SiR^1_cF_b$ where $R_f$ is a perfluoromethyl, perfluorethyl or perfluoropropyl group, $R^1$ is H or D, c is 0, 1, or 2, b is 1, 2, or 3, and c+b=1, 2, or 3, alkylsiloxysilanes of the formula $(R_3SiO)_{4-b}SiR_b$ where each R is independently H, D, F, methyl, ethyl or propyl, and b is 1, 2 or 3, alkoxysilanes of the formula $(R^2O)_{4-a}SiR^1_a$ where $R^2$ is methyl, ethyl or propyl, $R^1$ is H or D, and a is 0, 1, 2, or 3, alkylalkoxysilanes of the formula $(R^2O)_{4-c-b}SiR^2_bR^1_c$ where each $R^2$ is independently methyl, ethyl or propyl, $R^1$ is H or D, c is 0, 1, or 2, b is 1, 2, or 3, and c+b=1, 2, or 3, silylmethanes of the formula $(H_3Si)_{4-a}CR^1_a$ where $R^1$ is H or D, and a is 0, 1, 2, or 3, alkoxysilylmethanes of the formula $(R^2O)_{4-c-b}(H_3Si)_b CR^1_c$ where $R^2$ is methyl, ethyl or propyl, $R^1$ is H or D, c is 0, 1, or 2, b is 1, 2, or 3, and c+b=1, 2, or 3, alkylalkoxysilylmethanes of the formula $(R^2O)_{4-x-y-z}R^2_z(H_3Si)_yCR^1_x$ where each $R^2$ is independently methyl, ethyl or propyl, $R^1$ is H or D, x is 0 or 1, y is 1 or 2, z is 1 or 2, and x+y+z=2 or 3, alkoxymethanes of the formula $(R^3O)_{4-a}CR^1_a$ where $R^3$ is methyl, ethyl, propyl, or t-butyl, $R^1$ is H or D, and a is 0, 1, 2, or 3, alkylalkoxymethanes of the formula $(R^3O)_{4-c-b}R^2_bCR^1_c$ where $R^3$ is methyl, ethyl, propyl, or t-butyl, $R^2$ is methyl, ethyl or propyl, $R^1$ is H or D, c is 0, 1, or 2, b is 1, 2, or 3, and c+b=1, 2, or 3, and mixtures thereof.

35. The chemical vapor deposition process of claim 27 wherein said second chemical precursor contains Si and C.

36. The chemical vapor deposition process of claim 27 wherein said second gas is further comprised of a third chemical precursor selected from the group consisting of silane, disilane, trisilane, methane, ethane, propane, butane, oxygen, ozone, hydrogen peroxide, nitrous oxide and water.

37. The chemical vapor deposition process of claim 27 wherein said first Si-containing film and said second Si-containing film each independently have a thickness in the range of about 150 Å to about 2500 Å.

38. The chemical vapor deposition process of claim 27 which further comprises introducing a third gas to said chamber, wherein said third gas is comprised of a third chemical precursor different from said second chemical precursor, and depositing a third Si-containing film onto said second Si-containing film to provide a multi-layered Si-containing film having at least three layers, wherein said third Si-containing film has a dielectric constant of about 3.5 or lower, as deposited, and wherein said third Si-containing film has a thickness in the range of about 50 Å to about 500 Å.

39. The chemical vapor deposition process of claim 38 wherein said multi-layered Si-containing film having at least three layers has a dielectric constant of about 3.0 or lower.

40. The chemical vapor deposition process of claim 38 wherein said multi-layered Si-containing film having at least three layers has a dielectric constant of about 2.7 or lower.

41. The chemical vapor deposition process of claim 38 wherein said multi-layered Si-containing film having at least three layers has a dielectric constant of about 2.5 or lower.

42. The chemical vapor deposition process of claim 38 wherein said first Si-containing film is deposited by thermal chemical vapor deposition at a temperature of about 300° C. or higher.

43. The chemical vapor deposition process of claim 42 wherein said temperature is in the range of about 350° C. to about 700° C.

44. The chemical vapor deposition process of claim 42 wherein said temperature is in the range of about 400° C. to about 550° C.

45. The chemical vapor deposition process of claim 38 wherein said first Si-containing film, said second Si-containing film and said third Si-containing film each independently have a thickness in the range of about 150 Å to about 2500 Å.

* * * * *